(12) United States Patent
Itoh

(10) Patent No.: US 10,658,082 B2
(45) Date of Patent: May 19, 2020

(54) INFORMATION PROCESSING APPARATUS, INFORMATION PROCESSING SYSTEM, AND METHOD FOR PROVIDING INFORMATION

(71) Applicant: Masahiko Itoh, Kanagawa (JP)

(72) Inventor: Masahiko Itoh, Kanagawa (JP)

(73) Assignee: Ricoh Company, Ltd., Tokyo (JP)

(*) Notice: Subject to any disclaimer, the term of this patent is extended or adjusted under 35 U.S.C. 154(b) by 269 days.

(21) Appl. No.: 15/244,186

(22) Filed: Aug. 23, 2016

(65) Prior Publication Data
US 2017/0061090 A1 Mar. 2, 2017

(30) Foreign Application Priority Data
Sep. 2, 2015 (JP) .................. 2015-173019

(51) Int. Cl.
G16H 40/63 (2018.01)
H04W 4/029 (2018.01)

(52) U.S. Cl.
CPC ............ *G16H 40/63* (2018.01); *H04W 4/029* (2018.02)

(58) Field of Classification Search
None
See application file for complete search history.

(56) References Cited

U.S. PATENT DOCUMENTS

2007/0267475 A1* 11/2007 Hoglund ................ G06Q 10/10
235/375
2008/0233925 A1* 9/2008 Sun ......................... H04L 67/12
455/414.1

(Continued)

FOREIGN PATENT DOCUMENTS

JP 2003-323490 11/2003
JP 2005-173723 6/2005

(Continued)

OTHER PUBLICATIONS

Boulos et al, Real-time locating systems (RTLS) in healthcare: a condensed primer, Int. J. of Health Geographics, 2012, 11:25, pp. 1-8 (Year: 2012).*

(Continued)

*Primary Examiner* — Dennis W Ruhl
*Assistant Examiner* — William G Lultschik
(74) *Attorney, Agent, or Firm* — IPUSA, PLLC

(57) ABSTRACT

An information processing apparatus is connected via a network with an external server that manages identification information of wireless apparatuses in a facility, and information about detector apparatuses that detect identification information of the wireless apparatuses. The information processing apparatus includes a circuitry, in communication with a memory, that executes steps of associating the identification information of the wireless apparatus attached to a patient in the facility, with information about a medical care of the patient, to manage the associated information; obtaining the identification information of the wireless apparatus, and the information about the detector apparatus from the external server; managing positional information of the wireless apparatus attached to the patient by using the obtained information; and providing the medical information about the patient having the wireless apparatus attached, by using the positional information of the wireless apparatus attached to the patient.

21 Claims, 34 Drawing Sheets

(56) References Cited

U.S. PATENT DOCUMENTS

| | | | | |
|---|---|---|---|---|
| 2009/0102612 A1* | 4/2009 | Dalbow | ............... | A61N 5/1048 340/10.4 |
| 2009/0212956 A1* | 8/2009 | Schuman | ............... | G08B 5/222 340/573.1 |
| 2009/0315735 A1* | 12/2009 | Bhavani | ................ | G06Q 10/06 340/8.1 |
| 2010/0204999 A1* | 8/2010 | Scarola | .................... | G01S 5/02 705/2 |
| 2011/0071850 A1 | 3/2011 | Nuthi | | |
| 2013/0311516 A1* | 11/2013 | Callans | ................. | G16H 40/20 707/798 |
| 2014/0006943 A1* | 1/2014 | Robbins | ................ | G06Q 50/22 715/273 |
| 2014/0297371 A1* | 10/2014 | Colburn | .................. | G07C 1/10 705/7.38 |
| 2015/0082542 A1* | 3/2015 | Hayes | ................... | A61G 7/018 5/600 |
| 2015/0123791 A1* | 5/2015 | Greenberg | ............ | G01S 5/0263 340/539.13 |
| 2016/0012196 A1* | 1/2016 | Mark | .................... | G06Q 10/00 705/2 |

FOREIGN PATENT DOCUMENTS

| | | |
|---|---|---|
| JP | 2009-198209 | 9/2009 |
| JP | 2010-204872 | 9/2010 |
| JP | 2011-070668 | 4/2011 |
| JP | 2013-148972 | 8/2013 |

OTHER PUBLICATIONS

Japanese Office Action for 2015-173019 dated Jun. 4, 2019.

* cited by examiner

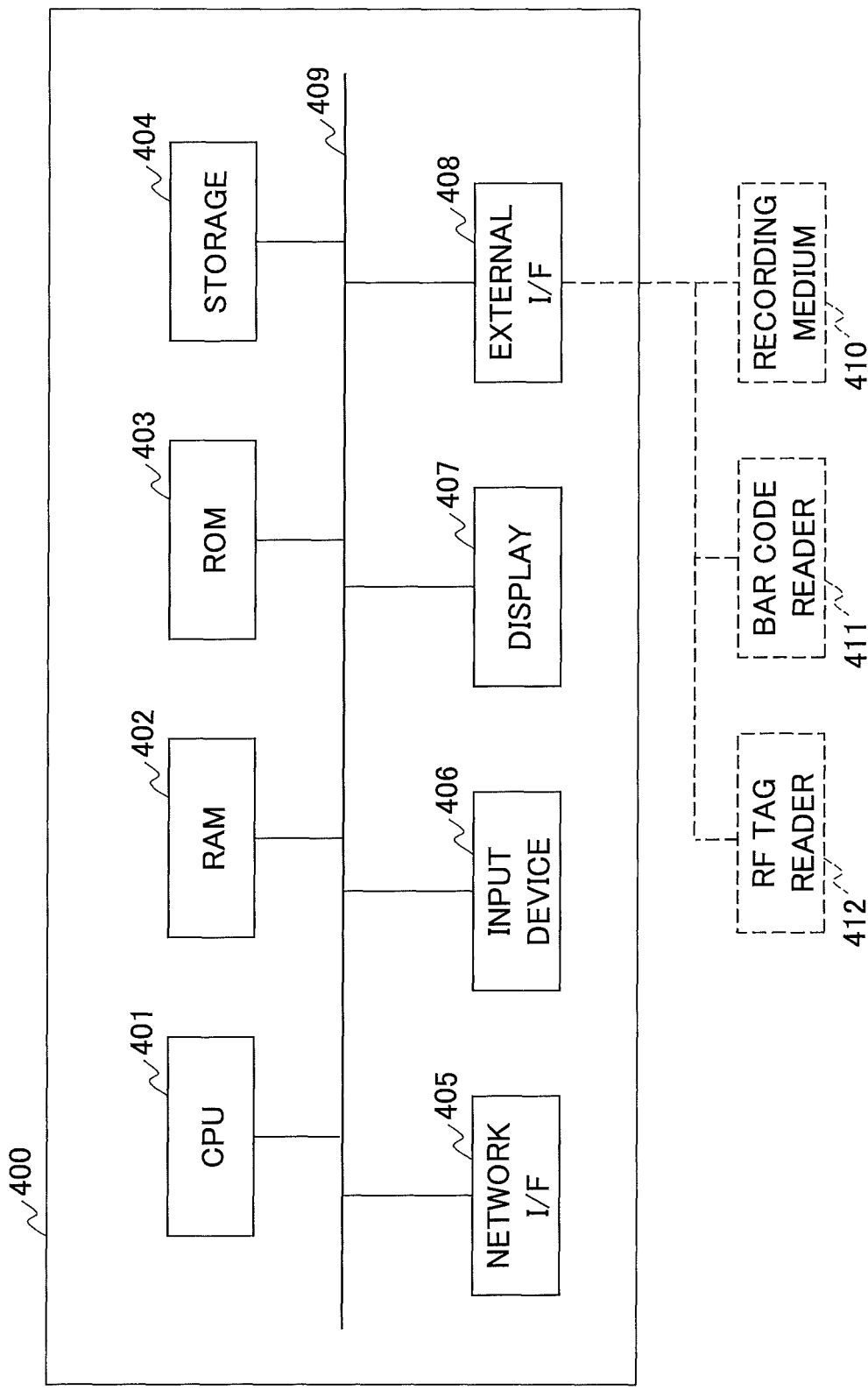

FIG.9A

| DATE | WIRELESS TAG ID | DETECTOR ID | DETECTED TIME | ... |
|---|---|---|---|---|
| ... | ... | ... | ... | ... |
| 20xx.10.01 | TAG101001 | 0005 | 9:45 | ... |
| | | 0005 | 9:40 | ... |
| | | 0005 | 9:35 | ... |
| | | 0005 | 9:30 | ... |
| | | ... | ... | ... |
| | ... | ... | ... | ... |
| | TAG101003 | 0020 | 9:46 | ... |
| | | 0020 | 9:45 | ... |
| | | 0020 | 9:38 | ... |
| | | 0029 | 9:36 | ... |
| | | 0028 | 9:35 | ... |
| | | 0027 | 9:34 | ... |
| | | 0026 | 9:33 | ... |
| | | 0007 | 9:30 | ... |
| | | ... | ... | ... |
| | ... | ... | ... | ... |
| ... | ... | ... | ... | ... |

| TIME | WIRELESS TAG ID | DETECTOR ID |
|---|---|---|
| ... | ... | ... |
| 9:45 | 101000001 | 0005 |
| 9:45 | 101000002 | 0006 |
| 9:46 | 101000003 | 0020 |
| 9:45 | 101000004 | 0008 |
| 9:45 | 101000005 | 0010 |
| ... | ... | ... |

FIG.9C

| DATE | TIME | WIRELESS TAG ID | DETECTOR ID |
|---|---|---|---|
| 20xx.10.01 | 9:30 | ... | ... |
| | | 101000001 | 0005 |
| | | 101000002 | 0006 |
| | | 101000003 | 0007 |
| | | 101000004 | 0008 |
| | | 101000005 | 0010 |
| | | ... | ... |

FIG.10

| PATIENT ID | BAR CODE ID | NAME | DATE OF BIRTH | CLINICAL DEPARTMENT | CONDITION INFORMATION | PLANNED DATA AND TIME OF TREATMENT | PLACE OF TREATMENT | CHART INFORMATION |
|---|---|---|---|---|---|---|---|---|
| ... | ... | ... | ... | ... | ... | ... | ... | ... |
| PID3001 | xxxxxxx000001 | XX | yy.mm.dd | INTERNAL MEDICINE | INFECTIOUS DISEASE, NO VISITORS ALLOWED | 20xx.10.1 13:40-13:50 | PRIVATE ROOM A | Link_C1 |
| PID3002 | xxxxxxx000002 | YY | yy.mm.dd | INTERNAL MEDICINE | TO LEAVE ON 10/1 | - | - | Link_C2 |
| PID3003 | xxxxxxx000003 | ZZ | yy.mm.dd | SURGERY | REST REQUIRED | 20xx.10.1 13:00-13:10 | PRIVATE ROOM C | Link_C3 |
| PID3004 | xxxxxxx000004 | AA | yy.mm.dd | SURGERY | HOSPITALIZED ON 10/1 | - | - | Link_C4 |
| PID3005 | xxxxxxx000005 | BB | yy.mm.dd | SURGERY | FEVERISH | 20xx.10.1 13:20-13:30 | FOUR-BED ROOM A | Link_C5 |
| ... | ... | ... | ... | ... | ... | ... | ... | ... |

| WIRELESS TAG ID | BAR CODE ID |
|---|---|
| ... | ... |
| 101000001 | xxxxxxx000001 |
| 101000002 | xxxxxxx000002 |
| 101000003 | xxxxxxx000003 |
| 101000004 | xxxxxxx000004 |
| 101000005 | xxxxxxx000005 |
| ... | ... |

| WIRELESS TAG ID | PATIENT ID | BAR CODE ID | NAME | DATE OF BIRTH | CLINICAL DEPARTMENT | CONDITION INFORMATION | PLANNED DATA AND TIME OF TREATMENT | PLACE OF TREATMENT | CHART INFORMATION |
|---|---|---|---|---|---|---|---|---|---|
| ... | ... | ... | ... | ... | ... | ... | ... | ... | ... |
| 101000001 | PID3001 | xxxxxxx000001 | XX | yy.mm.dd | INTERNAL MEDICINE | INFECTIOUS DISEASE, NO VISITORS ALLOWED | 20xx.10.1 13:40-13:50 | PRIVATE ROOM A | Link_C1 |
| 101000002 | PID3002 | xxxxxxx000002 | YY | yy.mm.dd | INTERNAL MEDICINE | TO LEAVE ON 10/1 | - | - | Link_C2 |
| 101000003 | PID3003 | xxxxxxx000003 | ZZ | yy.mm.dd | SURGERY | REST REQUIRED | 20xx.10.1 13:00-13:10 | PRIVATE ROOM C | Link_C3 |
| 101000004 | PID3004 | xxxxxxx000004 | AA | yy.mm.dd | SURGERY | HOSPITALIZED ON 10/1 | - | - | Link_C4 |
| 101000005 | PID3005 | xxxxxxx000005 | BB | yy.mm.dd | SURGERY | FEVERISH | 20xx.10.1 13:20-13:30 | FOUR-BED ROOM A | Link_C5 |
| ... | ... | ... | ... | ... | ... | ... | ... | ... | ... |

FIG.12A

| DETECTOR ID | FLOOR NAME | AREA INFORMATION | ROOM INFORMATION | LAYOUT DIAGRAM | PLACEMENT INFORMATION |
|---|---|---|---|---|---|
| ... | ... | ... | ... | ... | ... |
| 0005 | 3F | 5TH AREA | PRIVATE ROOM A | Link_M3 | Link_L3 |
| 0006 | 3F | 6TH AREA | PRIVATE ROOM B | Link_M3 | Link_L3 |
| 0020 | 3F | 20TH AREA | DAY ROOM | Link_M3 | Link_L3 |
| 0008 | 3F | 8TH AREA | FOUR-BED ROOM A | Link_M3 | Link_L3 |
| 0010 | 3F | 10TH AREA | FOUR-BED ROOM A | Link_M3 | Link_L3 |
| ... | ... | ... | ... | ... | ... |

| TIME | WIRELESS TAG ID | DETECTOR ID | FLOOR NAME | AREA INFORMATION | ROOM INFORMATION | LAYOUT DIAGRAM | PLACEMENT INFORMATION |
|---|---|---|---|---|---|---|---|
| ... | ... | ... | ... | ... | ... | ... | ... |
| 09:45 | 101000001 | 5 | 3F | 5TH AREA | PRIVATE ROOM A | Link_M3 | Link_L3 |
| 09:45 | 101000002 | 6 | 3F | 6TH AREA | PRIVATE ROOM B | Link_M3 | Link_L3 |
| 09:45 | 101000003 | 20 | 3F | 20TH AREA | DAY ROOM | Link_M3 | Link_L3 |
| 09:45 | 101000004 | 8 | 3F | 8TH AREA | FOUR-BED ROOM A | Link_M3 | Link_L3 |
| 09:45 | 101000005 | 10 | 3F | 10TH AREA | FOUR-BED ROOM A | Link_M3 | Link_L3 |
| ... | ... | ... | ... | ... | ... | ... | ... |

811

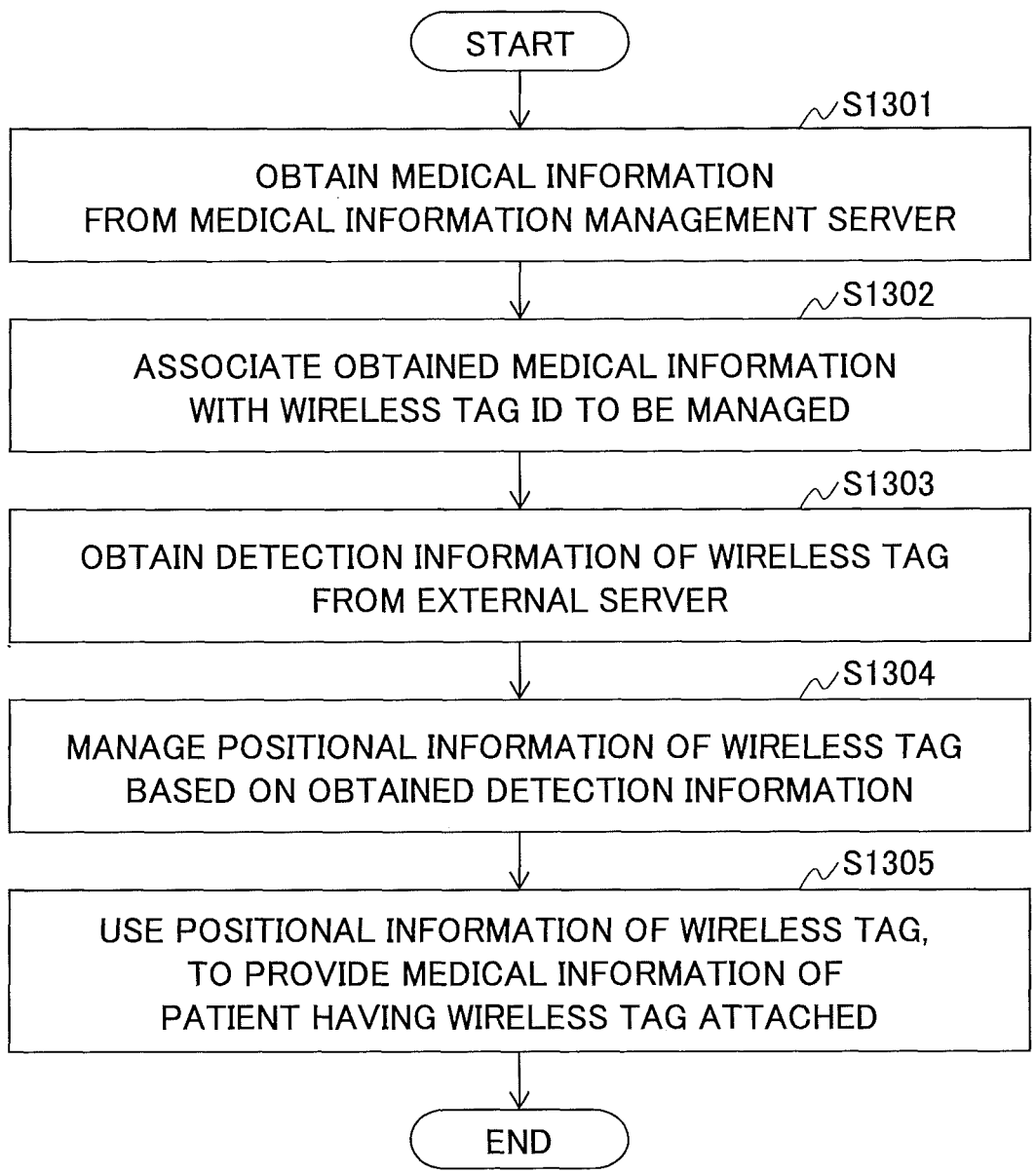

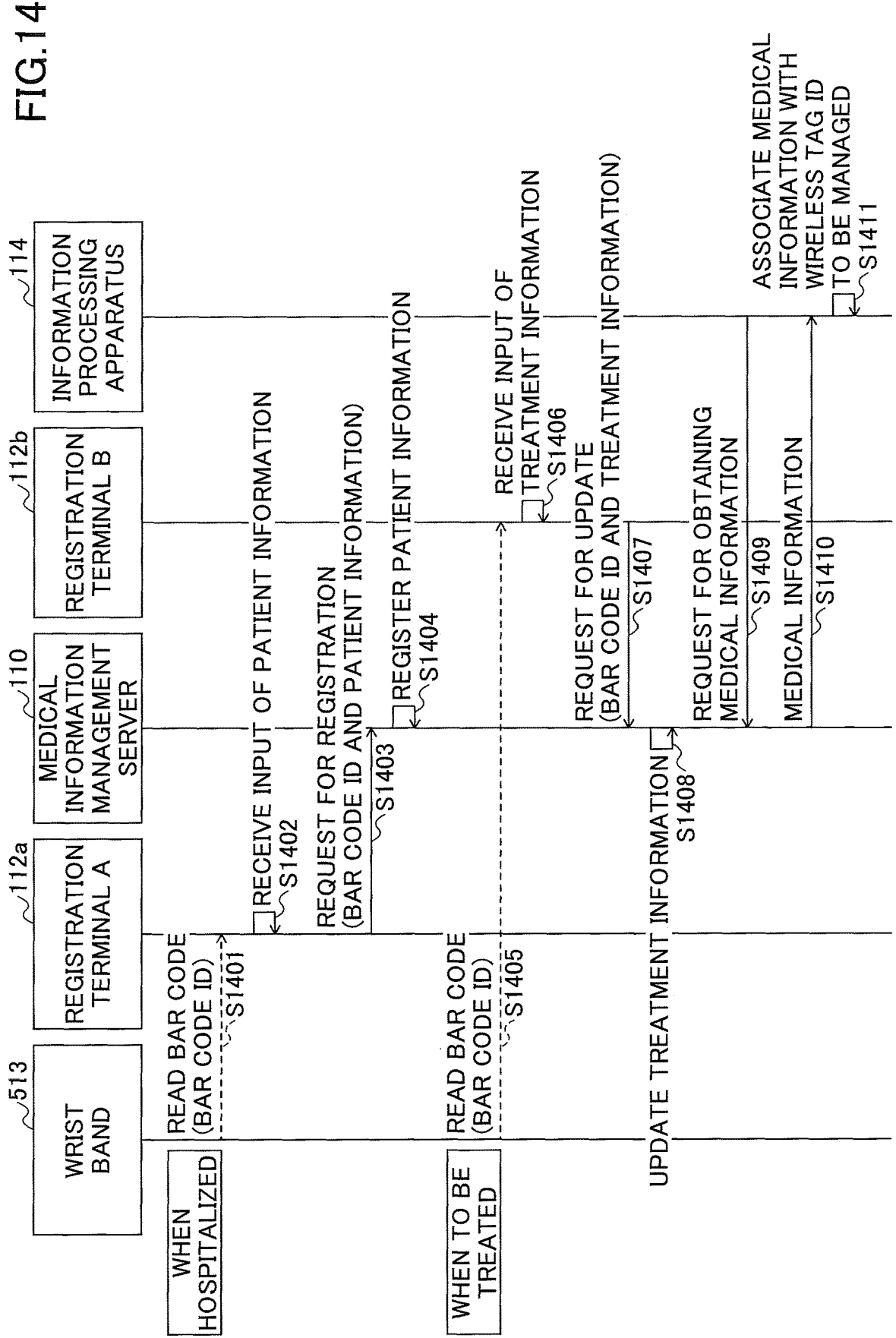

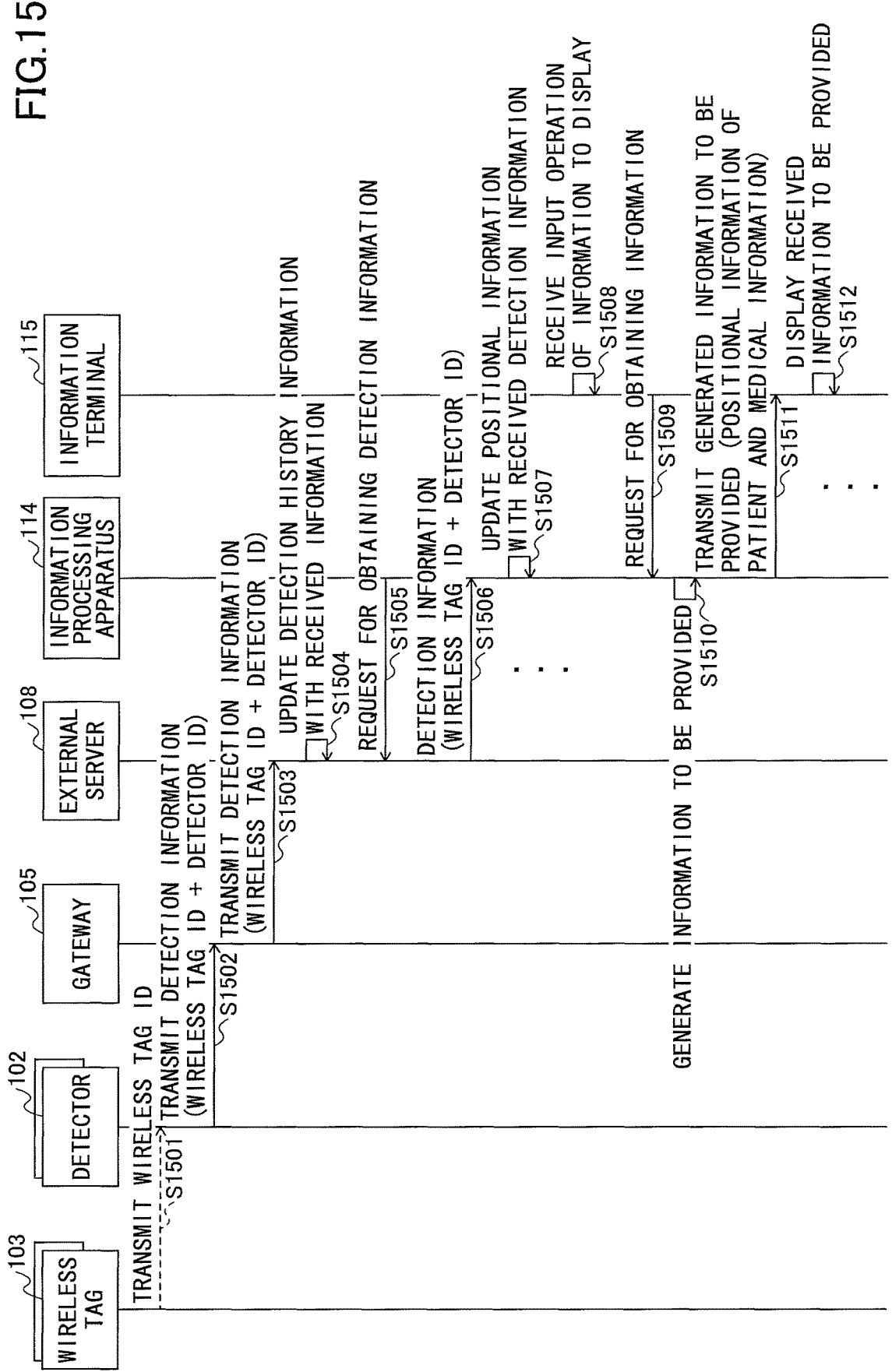

FIG.20A

| WIRELESS TAG ID | BAR CODE ID | DOCTOR ID | NURSE ID | DRUG ID |
|---|---|---|---|---|
| ⋮ | ⋮ | ⋮ | ⋮ | ⋮ |
| 101000001 | xxxxxx000001 | — | — | — |
| 101000002 | xxxxxx000002 | — | — | — |
| ⋮ | ⋮ | ⋮ | ⋮ | ⋮ |
| 102000101 | — | DID1001 | — | — |
| 102000102 | — | DID1002 | — | — |
| ⋮ | ⋮ | ⋮ | ⋮ | ⋮ |
| 103000201 | — | — | NID2001 | — |
| 103000202 | — | — | NID2002 | — |
| ⋮ | ⋮ | ⋮ | ⋮ | ⋮ |
| 501000001 | — | — | — | MID5001 |
| 501000002 | — | — | — | MID5002 |

| WIRELESS TAG ID OF PATIENT | PATIENT ID | BAR CODE ID | NAME OF PATIENT | PLANNED DATA AND TIME OF TREATMENT | PLANNED PLACE OF TREATMENT | MEDICAL PRACTITIONER ID | WIRELESS TAG ID OF MEDICAL PRACTITIONER | ADMINISTERED DRUG ID | WIRELESS TAG ID OF DRUG |
|---|---|---|---|---|---|---|---|---|---|
| ... | ... | ... | ... | ... | ... | ... | ... | ... | ... |
| 101000001 | PID3001 | xxxxxx000001 | XX | 20xx.10.1 13:40-13:50 | PRIVATE ROOM A (0005) | DID1001 | 102000101 | MID5002 | 501000002 |
| 101000002 | PID3002 | xxxxxx000002 | YY | - | - | - | - | - | - |
| 101000003 | PID3003 | xxxxxx000003 | ZZ | 20xx.10.1 13:00-13:10 | PRIVATE ROOM C (0007) | NID2001 | 103000201 | MID5001 | 501000001 |
| 101000004 | PID3004 | xxxxxx000004 | AA | - | - | - | - | - | - |
| 101000005 | PID3005 | xxxxxx000005 | BB | 20xx.10.1 13:20-13:30 | FOUR-BED ROOM A (0010) | NID2002 | 103000202 | MID5002 | 501000002 |
| ... | ... | ... | ... | ... | ... | ... | ... | ... | ... |

809

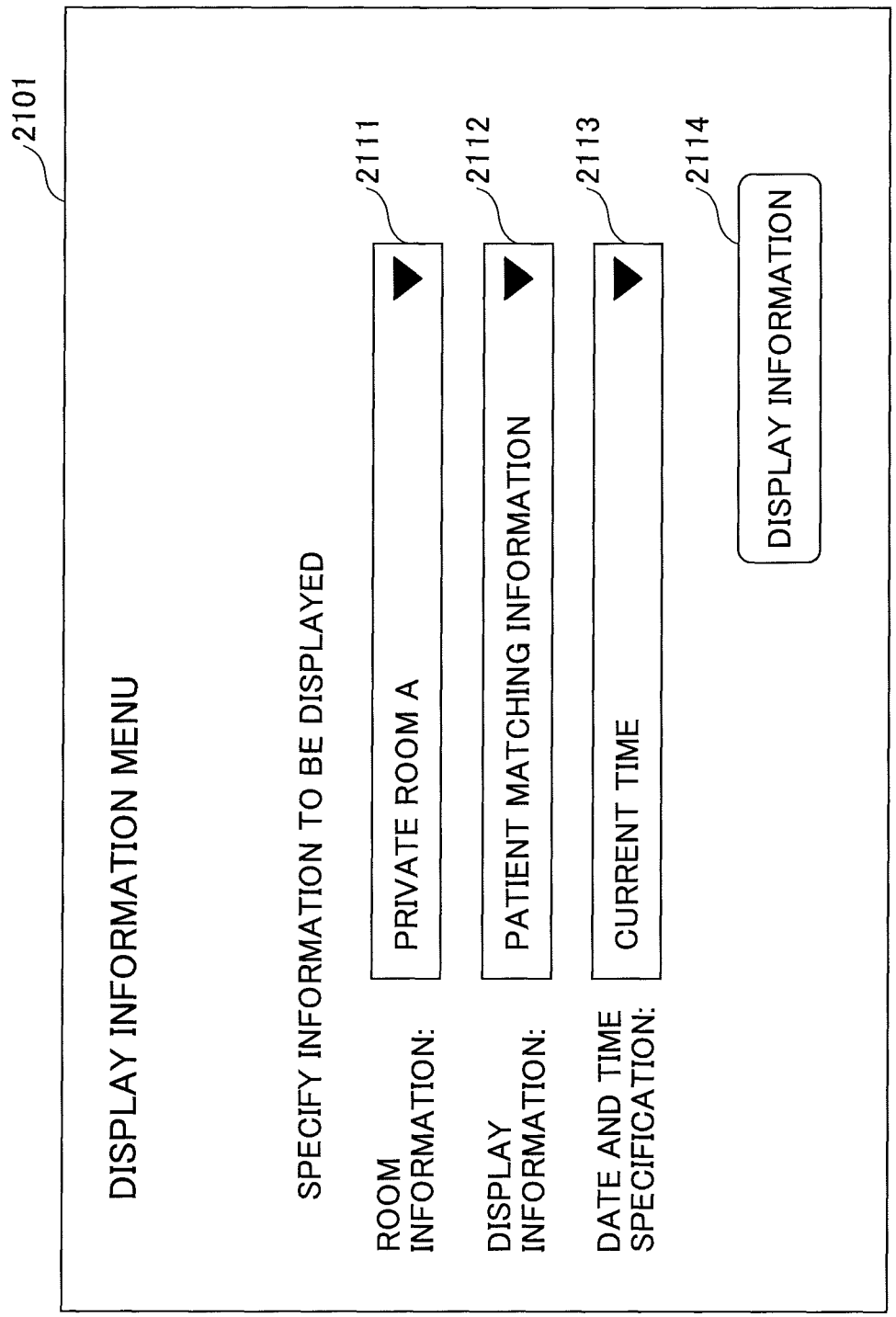

PATIENT MATCHING INFORMATION

ROOM NAME: PRIVATE ROOM A

DATE AND TIME: 20xx.10.1 13:41

WIRELESS TAG ID OF PATIENT TO BE TREATED: 101000001

WIRELESS TAG ID OF PATIENT IN PRIVATE ROOM A: 101000001

DETERMINATION RESULT: OK

[CONFIRM]

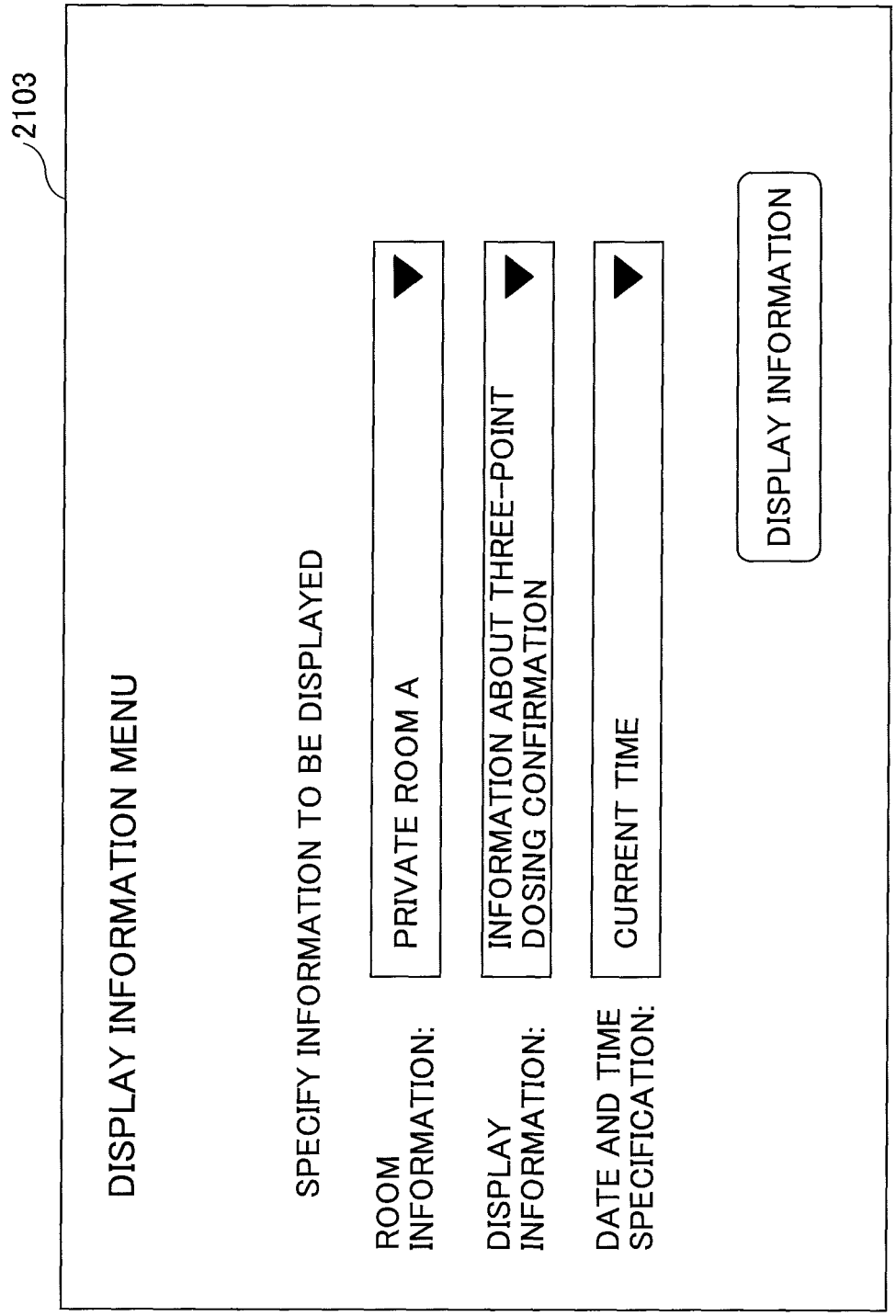

FIG.21D

INFORMATION ABOUT THREE-POINT DOSING CONFIRMATION — 2104

ROOM NAME: PRIVATE ROOM A

DATE AND TIME: 20xx.10.1 13:41

WIRELESS TAG ID OF PATIENT: MATCHED

WIRELESS TAG ID OF MEDICAL PRACTITIONER: MATCHED

WIRELESS TAG ID OF DRUG: MATCHED

DETERMINATION RESULT: OK

[CONFIRM]

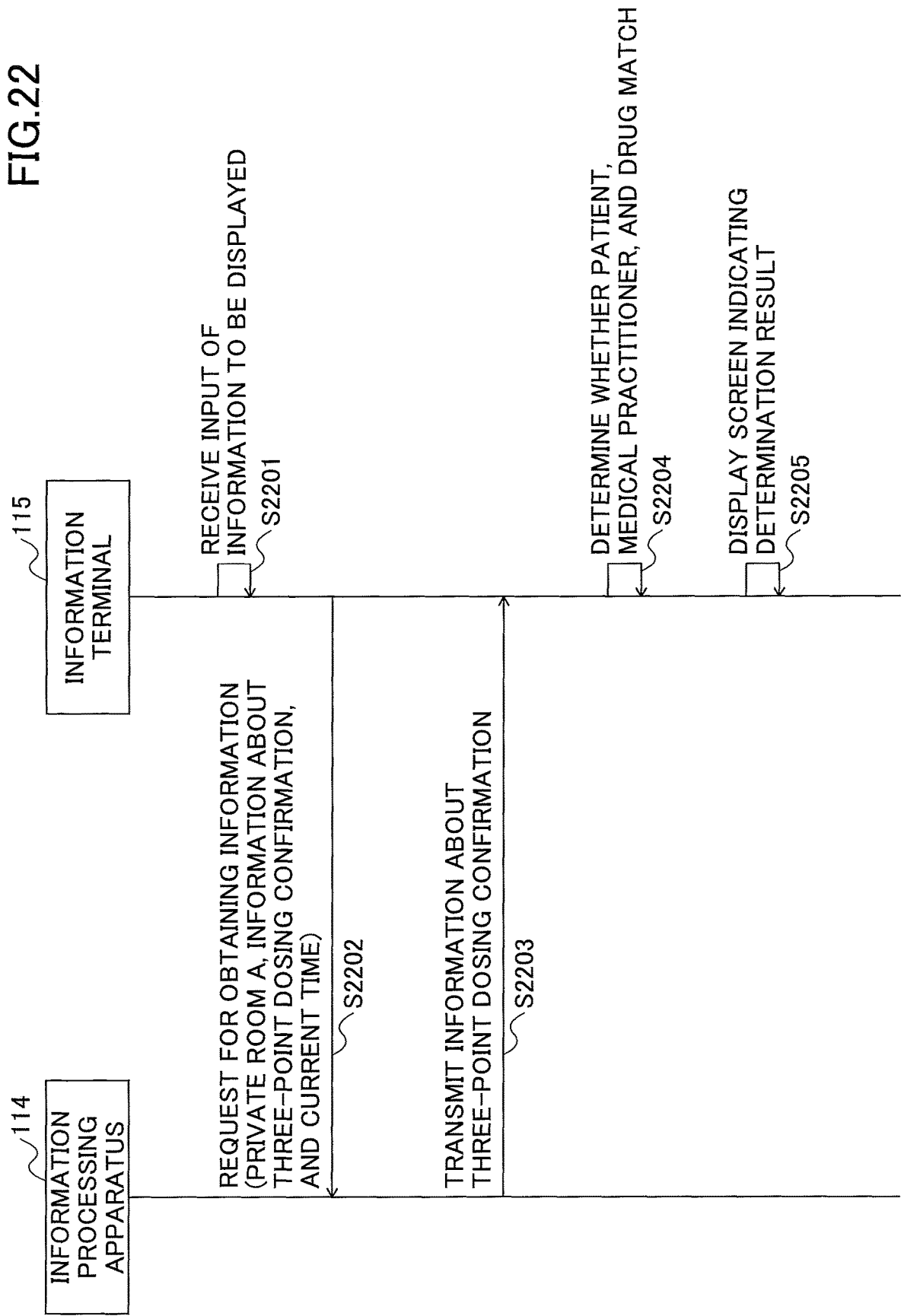

FIG.23

| WIRELESS TAG ID | BAR CODE ID | DOCTOR ID | NURSE ID | DRUG ID | DEVICE ID | ... |
|---|---|---|---|---|---|---|
| ... | ... | ... | ... | ... | ... | ... |
| 101000001 | xxxxxx000001 | — | — | — | — | ... |
| 101000002 | xxxxxx000002 | — | — | — | — | ... |
| ... | ... | ... | ... | ... | ... | ... |
| 102000101 | — | DID1001 | — | — | — | ... |
| 102000102 | — | DID1002 | — | — | — | ... |
| ... | ... | ... | ... | ... | ... | ... |
| 103000201 | — | — | NID2001 | — | — | ... |
| 103000202 | — | — | NID2002 | — | — | ... |
| ... | ... | ... | ... | ... | ... | ... |
| 501000001 | — | — | — | MID5001 | — | ... |
| 501000002 | — | — | — | MID5002 | — | ... |
| ... | ... | ... | ... | ... | ... | ... |
| 601000001 | — | — | — | — | AID6001 | ... |
| 601000002 | — | — | — | — | AID6002 | ... |
| ... | ... | ... | ... | ... | ... | ... |

| OPERATION ID | OPERATION ROOM | PLANNED DATA AND TIME OF OPERATION | PATIENT ID | WIRELESS TAG ID OF PATIENT | DOCTOR ID | WIRELESS TAG ID OF DOCTOR | NURSE ID | WIRELESS TAG ID OF NURSE | DEVICE ID | WIRELESS TAG ID OF DEVICE |
|---|---|---|---|---|---|---|---|---|---|---|
| ... | ... | ... | ... | ... | ... | ... | ... | ... | ... | ... |
| OID0001 | OPERATING ROOM A | 20xx.10.1 9:00–10:00 | PID3012 | 101000012 | DID1001 | 102000101 | NID2001 | 103000201 | AID6001 | 601000001 |
| OID0002 | OPERATING ROOM A | 20xx.10.1 15:30–16:50 | PID3014 | 101000014 | DID1002 | 102000102 | NID2002 | 103000202 | AID6002 | 601000002 |
| ... | ... | ... | ... | ... | ... | ... | ... | ... | ... | ... |

OPERATION MATCHING INFORMATION

ROOM NAME: PRIVATE ROOM A

DATE AND TIME: 20xx.10.1 13:45

WIRELESS TAG ID OF PATIENT: MATCHED

WIRELESS TAG ID OF DOCTOR: MATCHED

WIRELESS TAG ID OF NURSE: MATCHED

WIRELESS TAG ID OF DEVICE: MATCHED

DETERMINATION RESULT: OK

END

FIG.25C

OPERATION MATCHING INFORMATION ~2503

ROOM NAME: PRIVATE ROOM A

DATE AND TIME: 20xx.10.1 13:50

WIRELESS TAG ID OF PATIENT: MATCHED

WIRELESS TAG ID OF DOCTOR: MATCHED

WIRELESS TAG ID OF NURSE: NOT MATCHED

WIRELESS TAG ID OF DEVICE: MATCHED

DETERMINATION RESULT: NG

[END]

FIG.26

DISPLAY INFORMATION MENU

SPECIFY INFORMATION TO BE DISPLAYED

DISPLAY INFORMATION: | PATIENT INFORMATION (CONDITION INFORMATION + PLANNED TREATMENT INFORMATION) ▶

FLOOR NAME: | 3F ▶

UPDATE INTERVAL: | NOT SPECIFIED ▶

DATE AND TIME SPECIFICATION: | 20xx.9.01 10:00 ▶

DISPLAY INFORMATION

2600

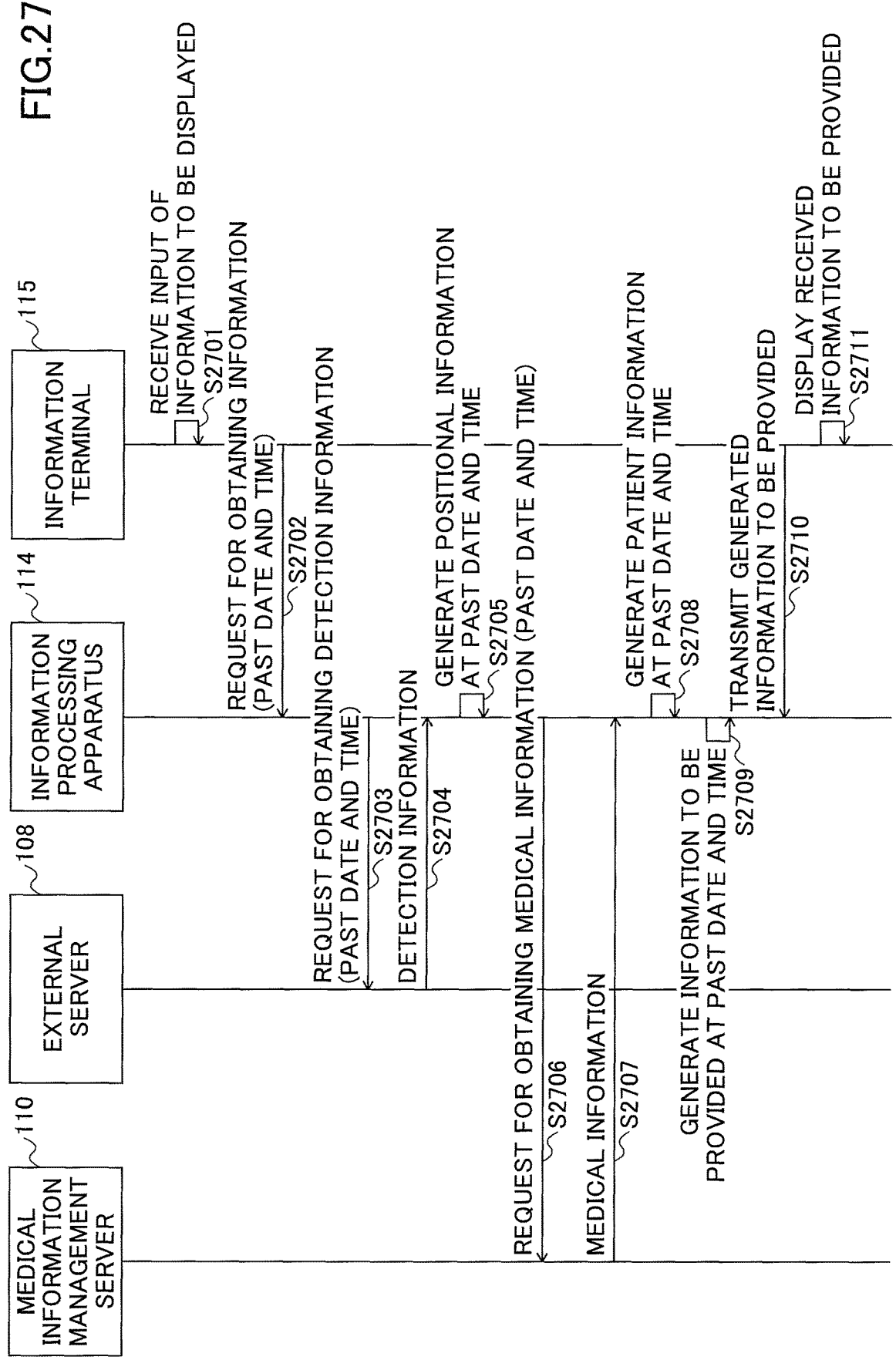

INFORMATION PROCESSING APPARATUS, INFORMATION PROCESSING SYSTEM, AND METHOD FOR PROVIDING INFORMATION

BACKGROUND OF THE INVENTION

1. Field of the Invention

The present disclosure relates to an information processing apparatus, an information processing system, and a method for providing information.

2. Description of the Related Art

In medical facilities such as hospitals, there have been demands for collectively managing, for example, positional information of hospitalized patients, and medical information about the patients (for example, charts, treatment times, and dosing times).

In this case, since a huge cost is required for installing and managing a positional information management system in a hospital, it is desirable that a medical information management system managing medical information can be built combined with a positional information management system provided by an external cloud service or the like.

However, information managed by a medical information management system includes a lot of information that should not be disclosed to the outside, for example, personal information of patients, information about treatments in the hospital, and layout information of sickrooms.

Therefore, difficulty accompanies providing both positional information and medical information, while preventing the medical information from leaking out.

SUMMARY OF THE INVENTION

According to an embodiment, an information processing apparatus is connected with an external server apparatus via a network. The external server apparatus manages identification information of a plurality of wireless apparatuses in a facility, and information about a plurality of detector apparatuses that detect identification information of the wireless apparatuses. The information processing apparatus includes a circuitry, in communication with a memory, executing steps of: associating the identification information of the wireless apparatus attached to a patient in the facility, with information about a medical care of the patient, to manage the associated information; obtaining the identification information of the wireless apparatus, and the information about the detector apparatus from the external server apparatus; managing positional information of the wireless apparatus attached to the patient by using the obtained information; and providing the medical information about the patient having the wireless apparatus attached, by using the positional information of the wireless apparatus attached to the patient.

BRIEF DESCRIPTION OF DRAWINGS

FIG. 4 is a diagram illustrating an example of a hardware configuration of a computer according to an embodiment;

FIGS. 9A-9C are diagrams illustrating an example of information managed by an external server according to the first embodiment;

FIG. 10 is a diagram illustrating an example of medical information managed by a medical information management server according to the first embodiment;

FIGS. 11A-11B are first diagrams illustrating an example of information managed by an information processing apparatus according to the first embodiment;

FIGS. 12A-12B are second diagrams illustrating an example of information managed by an information processing apparatus according to the first embodiment;

FIG. 13 is a flowchart illustrating an overview of a process of an information processing apparatus according to the first embodiment;

FIG. 14 is a sequence chart illustrating an example of a process for registration and update of medical information according to the first embodiment;

FIG. 15 is a sequence chart illustrating an example of a process for obtaining detection information and a process for providing information according to the first embodiment;

FIGS. 20A-20B are diagrams illustrating an example of information managed by an information processing apparatus according to a third embodiment;

FIGS. 21A-21D are diagrams illustrating examples of display screens on an information terminal according to the third embodiment;

FIG. 22 is a sequence chart illustrating an example of a process of an information processing system according to the third embodiment;

FIG. 23 is a diagram illustrating an example of associated information according to a fourth embodiment;

FIG. 24 is a diagram illustrating an example of patient information according to the fourth embodiment;

FIGS. 25A-25C are diagrams illustrating examples of display screens on an information terminal according to the fourth embodiment;

FIG. 26 is a diagram illustrating an example of a display screen on an information terminal according to a fifth embodiment; and FIG. 27 is a sequence chart illustrating an example of a process of an information processing system according to the fifth embodiment.

DETAILED DESCRIPTION OF THE EMBODIMENTS

In the following, embodiments will be described with reference to the drawings.

According to an embodiment in the present disclosure, it is possible to provide an information processing apparatus that makes it easy to provide positional information and medical information, by using a medical information management system and an external positional information management system while preventing the medical information from leaking out.

<Configuration of System>

First, a configuration of an information processing system will be described according to the embodiments.

Figure 1:
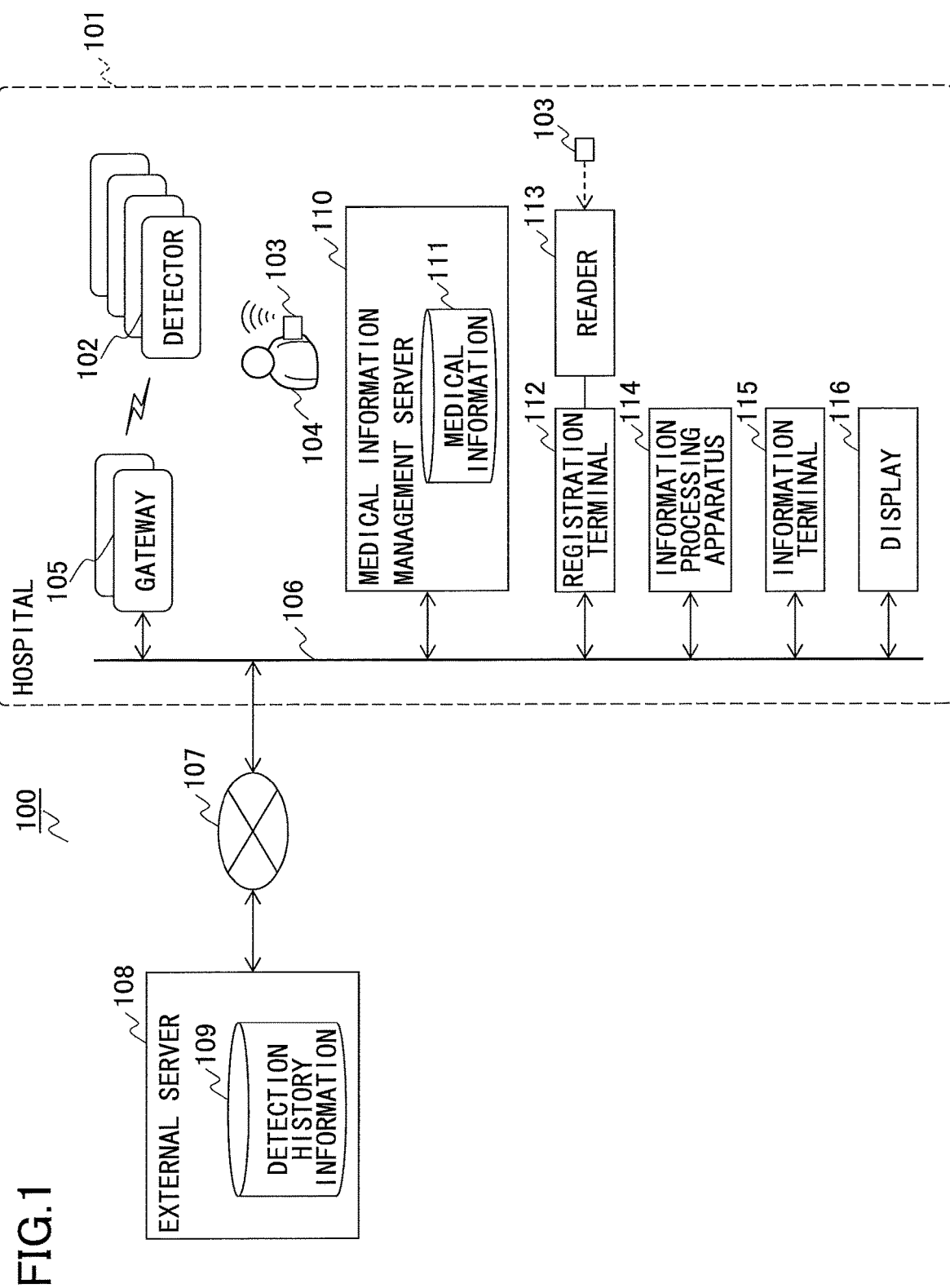
FIG. 1 is a diagram illustrating an example of a configuration of an information processing system according to an embodiment.

FIG. 1 is a diagram illustrating an example of a configuration of an information processing system 100 according to an embodiment. The information processing system 100 includes multiple detectors 102, a wireless tag 103, one or more gateways 105, an external server 108, a medical information management server 110, a registration terminal 112, a reader 113, an information processing apparatus 114, an information terminal 115, and a display 116.

As illustrated in FIG. 1, the gateway 105, the medical information management server 110, the registration terminal 112, the information processing apparatus 114, the information terminal 115, the display 116, and the like in the hospital 101 are connected with a network such as a LAN (Local Area Network) 106 or the like. Also, the external server 108 is connected with the LAN 106 in the hospital 101 via an external network such as the Internet 107 or the like.

The multiple detectors 102 are installed on the ceiling and the like in the hospital 101 at positions different from each other, and each detector 102 detects identification information of a wireless tag 103 (referred to as a "wireless tag ID", below) transmitted by the wireless tag 103 attached to a person 104 engaged in medical care in the hospital (for example, a patient, a doctor, and a nurse). Also, when detecting the wireless tag ID, the detector 102 transmits information about the detector 102 including the detected wireless tag ID and the identification information of the device itself (referred to as the "detector ID", below), to the external server 108 via the gateway 105. Note that the information about the detector 102 may be positional information about the detector 102.

Figure 2:
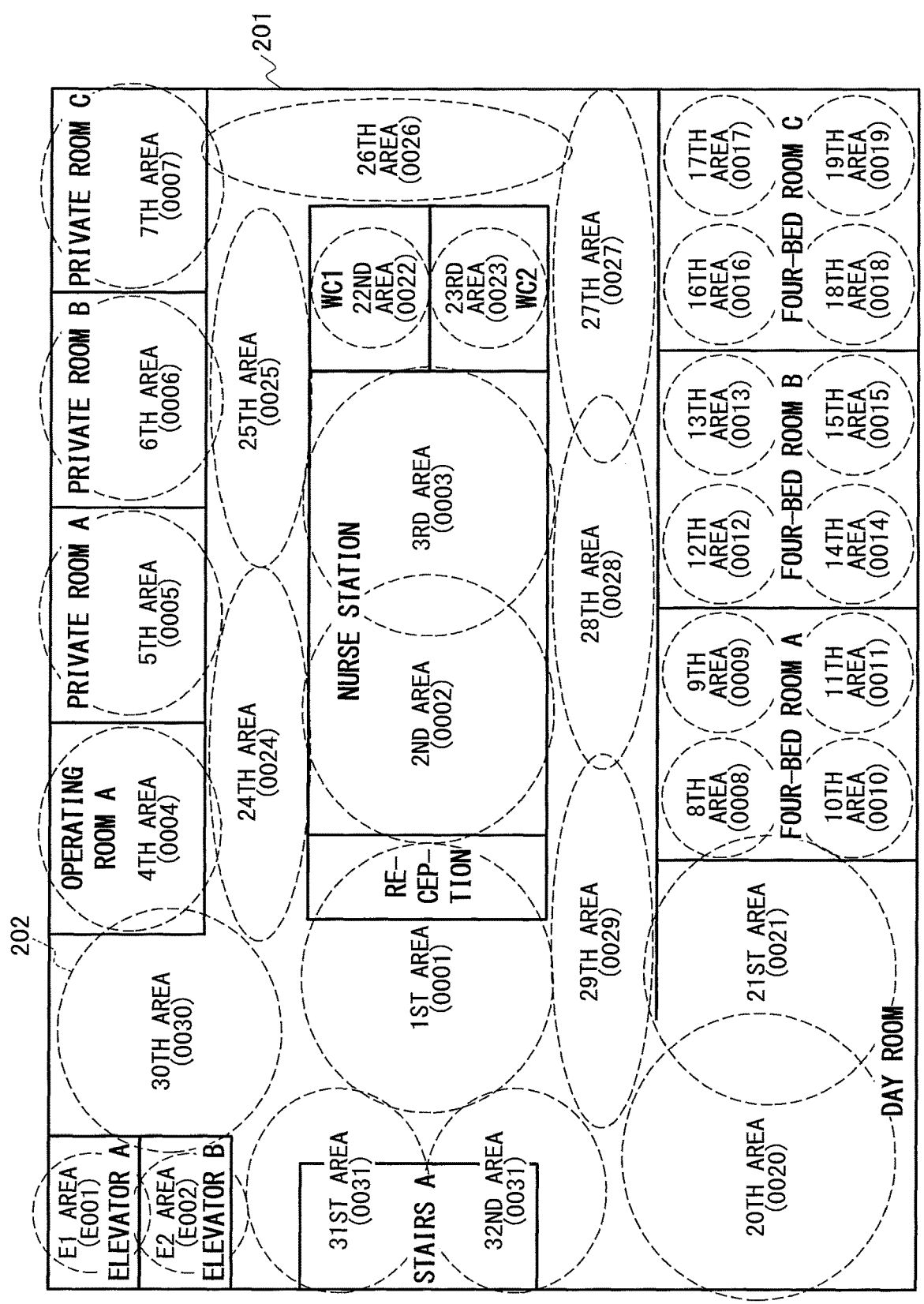
FIG. 2 is a diagram illustrating an example of a placement of detectors according to an embodiment.

FIG. 2 is a diagram illustrating an example of a placement of the detectors 102 according to an embodiment. FIG. 2 illustrates a layout diagram 201 as an example of a floor in the hospital 101, and detection ranges 202 of the respective detectors 102 installed on the floor (dashed-line circles and ellipses).

For example, a detector 102 is installed on the ceiling of the first area in front of the "reception" on the left side around the center of the layout diagram 201, to detect the wireless tag ID transmitted by the wireless tag 103 in the first area. Also, it is assumed that digits "0001" in parentheses designated below the "first area" represents the detector ID of the detector 102 disposed in the first area. When detecting (receiving) the wireless tag ID transmitted by the wireless tag 103, the detector 102 disposed in the first area transmits the detected wireless tag ID and the detector ID "0001" of the device itself to the external server 108 via the gateway 105.

It is assumed that sizes of the areas (the first to 31st areas) are set in advance depending on, for example, reception sensitivities and gains of antennas of the respective detectors 102, and shapes of the areas are set in advance depending on, for example, directional characteristics of the antennas of the detectors 102.

As illustrated in FIG. 2, it is desirable that the multiple detectors 102 are installed to cover the entire floor. This is because if there is a dead angle at which the wireless tag 103 cannot be detected, it is difficult to determine that no person 104 exists on this floor.

Also, for example, there are four-bed rooms A to C having four beds disposed, respectively. In such a case, it is desirable to have a detector 102 installed for each of the beds.

Referring back to FIG. 1, description of the system configuration will be continued.

The wireless tag 103 is a wireless apparatus attached to (or held by) a person 104 engaged in medical care, to transmit a wireless tag ID being the identification information of the device itself, for example, at predetermined time intervals (for example, every 30 seconds). The wireless tag 103 is an active RFID (Radio Frequency Identifier) tag or the like installed on, for example, a wrist band attached to a wrist of a patient being hospitalized, or a name plate, an identification card, or the like attached to a person engaged in medical care (a doctor, a nurse, a radiation technician, etc.) in the hospital 101.

Note that an active RFID tag is an example of the wireless tag 103. The wireless tag 103 may be another wireless apparatus, for example, an information terminal such as a smart phone, or a wearable terminal such as a smart watch.

The gateway 105 is a relay device that is capable of communicating with the multiple detectors 102 by a predetermined wireless communication protocol, and also capable of communicating with the external server 108 via a network such as the LAN 106 and the Internet 107. The gateway 105 relays transmission and reception of data between the multiple detectors 102 and the external server 108. This makes it possible for the multiple detectors 102 and the external server 108 to transmit and receive data via the gateway 105.

The external server 108 (an external server apparatus) is, for example, an information processing apparatus such as a PC, or a system that includes multiple information processing apparatuses. The external server 108 associates a wireless tag ID transmitted from one of the multiple detectors 102 with the detector ID, and stores and manages the associated IDs in the detection history information 109. Also, for example, in response to a request from the information processing apparatus 114, the external server 108 provides records of detection information (the wireless tag ID, the detector ID, and the like) about a wireless tag 103 to the information processing apparatus 114.

The medical information management server 110 is, for example, an information processing apparatus such as a PC, or a system that includes multiple information processing apparatuses. The medical information management server 110 stores and manages various information items about medical care in the hospital 101 (for example, chart information, information about inpatients, information about planned treatments) in medical information 111.

The registration terminal 112 is an information terminal, for example, a PC, a tablet terminal, or a smart phone.

For example, at the reception office for admission or the like in the hospital 101, a person in charge of reception uses the reader 113 connected to the registration terminal 112, to read a bar code or the like printed on a wrist band of a patient to be admitted. Also, the person in charge of reception uses the registration terminal 112, to input patient information including a patient ID as identification information of the patient to be admitted, the name, the date of birth, the clinical department, and the sickroom, and to execute a registration operation. Thus, the read bar code and the input patient information are transmitted to the medical information management server 110, and registered in the medical information 111.

Also, a doctor who has given a treatment to a patient uses the reader 113 and the like connected to the registration terminal 112, to read the bar code or the like printed on the wrist band of the patient. Also, the doctor inputs information about the treatment (the chart information and the like) into the registration terminal 112, and executes a registration operation. Thus, the read bar code and the input information about the treatment are transmitted to the medical information management server 110, and the information about the treatment of the patient registered in the medical information 111 is updated.

The information processing apparatus 114 obtains the medical information 111 managed by the medical information management server 110, associates the wireless tag ID of the wireless tag 103 attached to each patient, with the medical information about the patient, and manages the associated data. Also, the information processing apparatus 114 obtains records of detection information of the wireless tag 103 from the external server 108, and uses the obtained detection information, to manage positional information of the wireless tag 103 attached to the patient. Further, the information processing apparatus 114 uses positional information of the wireless tag 103 attached to the patient, to provide various medical information items about the patient having the wireless tag 103 attached.

Figure 3:
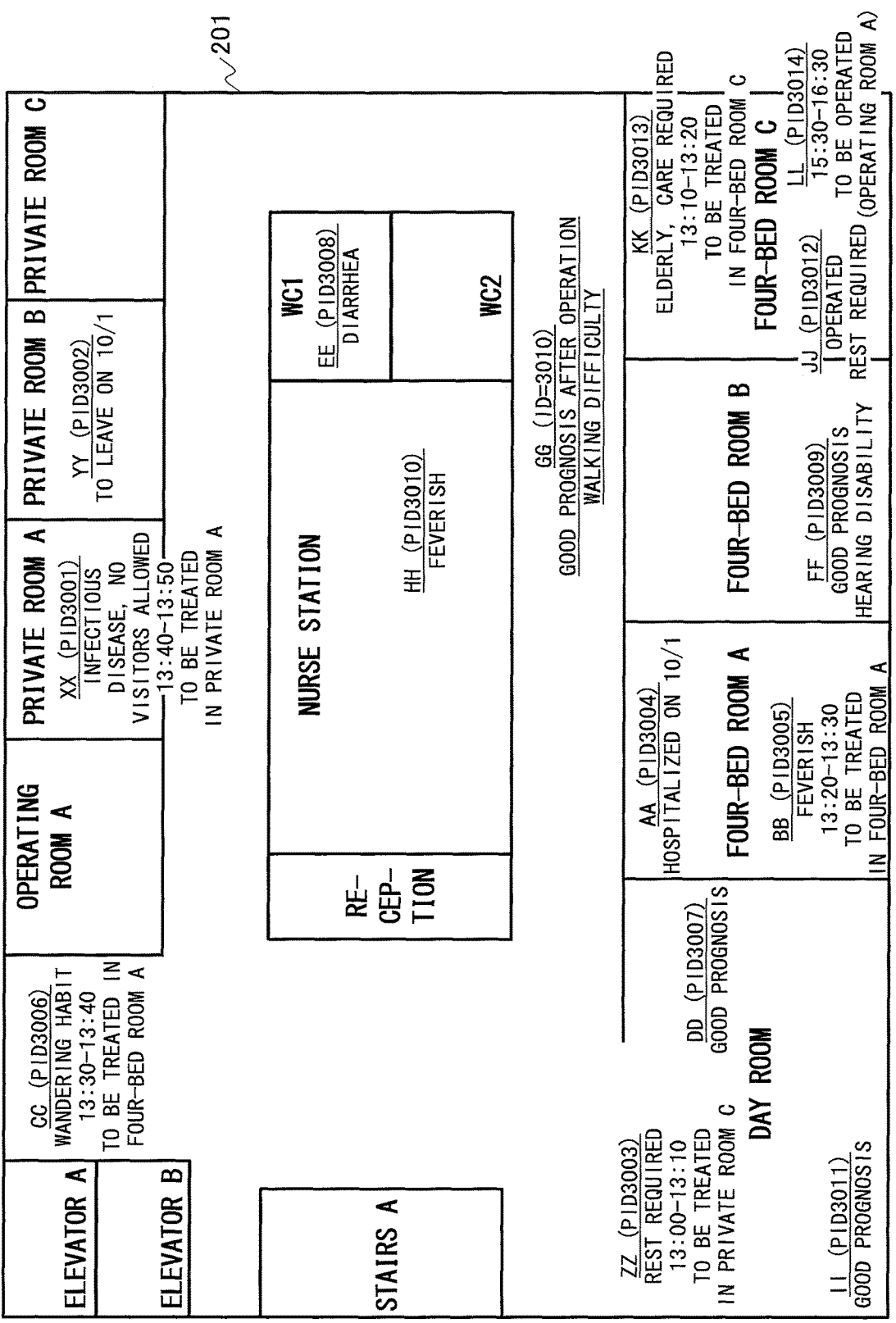
FIG. 3 is a diagram illustrating an example of information provided by an information processing apparatus according to an embodiment.

FIG. 3 is a diagram illustrating an example of information provided by an information processing apparatus according to an embodiment. In the example in FIG. 3, the layout diagram 201 as an example of the floor in the hospital 101 illustrates positions of patients, information about conditions of the patients, information about times when the patients receive treatments, and the like.

For example, in FIG. 3, information is displayed about a patient XX (having the patient ID "PID3001") being in the private room A, the conditions of the patient XX being "infectious disease" and "no visitors allowed", and to be treated in the private room A during 13:40 to 15:50.

Also, in the example in FIG. 3, information is displayed about a patient ZZ (having the patient ID "PID3003") being in the day room (a lounge or the like), the condition being "rest required", and to be treated in the private room C during 13:00 to 13:10. Such information makes it easier for a nurse or the like to prompt the patient ZZ to return to the private room C before 13:00.

Further, it is desirable that the information illustrated in FIG. 3 is updated at predetermined time intervals (for example, every minute). Thus, the nurse or the like can easily recognize, for example, a patient GG (having the patient ID "PID3010") proceeding in the corridor in a direction towards the "WC (Water Closet) 2", having the conditions of "good prognosis after operation" and "walking difficulty". Thus, the nurse or the like can come to the patient GG, for example, for helping the patient to walk.

Note that the diagram in FIG. 3 may be further configured to make it possible to read detailed information relevant to medical care of a patient (for example, the date of birth, the blood type, the chart information, etc.), for example, by selecting (for example, clicking) the name of the patient.

In this way, the information processing apparatus 114 according to the embodiment uses, for example, positional information of patients being hospitalized in the hospital 101, to be capable of providing not only information that represents the position of each patient, but also various information items about medical care of the patient (for example, the condition, the planned treatment time, etc.).

The information processing apparatus 114 transmits information as illustrated in FIG. 3 to, for example, the information terminal 115, the display 116, and the like, to be displayed. Alternatively, the information processing apparatus 114 may display information as illustrated in FIG. 3 on a display, a projector, or the like that is connected to the information processing apparatus 114.

Referring back to FIG. 1 again, description of the system configuration will be further continued.

The information terminal 115 is, for example, an information processing apparatus such as a PC, a tablet terminal, and a smart phone. The information terminal 115 uses, for example, an application program (referred to as an "application", below) or a web browser that is compatible with the information processing system 100, to display information provided by the information processing apparatus 114 (for example, information as illustrated in FIG. 3).

The display 116 is a display apparatus, for example, a display, a projector, a digital signage, or the like that may have a large size. The display 116 receives, for example, information as illustrated in FIG. 3, from the information processing apparatus 114, for example, as image data, and displays the information.

In this way, in the information processing system 100 according to the embodiment, the information processing apparatus 114 associates the wireless tag ID of the wireless tag attached to each patient, with information about medical care of the patient, and manages the associated data. Also, the information processing apparatus 114 uses detection information obtained from the external server 108, to manage positional information of the wireless tag attached to each patient, and uses the positional information of the wireless tag, to provide various medical information items about the patient having respective wireless tag attached.

In this case, information managed by the external server 108 only consists of wireless tag IDs and detector IDs.

Therefore, information managed by the medical information management server 110 such as the medical information 111 does not leak out to the outside of the hospital.

In this way, according to the embodiment, it is possible to provide the information processing apparatus 114 that makes it easy to provide positional information and medical information by using the medical information management server 110 and the external server 108 while preventing the medical information from leaking out.

<Hardware Configuration>

Next, a hardware configuration of each apparatus will be described.

(Hardware Configuration of Computer)

The external server 108, the medical information management server 110, the registration terminal 112, the information processing apparatus 114, the information terminal 115, and the like illustrated in FIG. 1 have a configuration of a generic computer.

FIG. 4 is a diagram illustrating an example of a hardware configuration of a computer 400 according to an embodiment. The computer 400 includes, for example, a CPU (Central Processing Unit) 401, a RAM (Random Access Memory) 402, a ROM (Read-Only Memory) 403, a storage 404, a network I/F (Interface) 405, an input device 406, a display 407, an external I/F 408, and a bus 409.

The CPU 401 is a processor to implement functions of the computer 400, by reading programs and data stored in the ROM 403 and the storage 404, to be loaded on the RAM 402, and executing processes. The RAM 402 is a volatile memory that is used as a work area of the CPU 401. The ROM 403 is a non-volatile memory that can hold programs and data even when the power is turned off.

The storage 404 is a mass storage device, for example, an HDD (Hard Disk Drive), or an SSD (Solid State Drive), to store an OS (Operation System), application programs, various data items, and the like.

The network I/F 405 is a communication interface to have the computer 400 connect with a network such as the LAN 106 and the Internet 107.

The input device 406 includes a pointing device such as a mouse, and a keyboard to be used for inputting operational signals into the computer 400.

The display 407 is a display apparatus to display processed results and the like by the computer 400.

The external I/F 408 is an interface with an external apparatus. The external apparatus includes, for example, a recording medium 410 and a reader 113 such as a bar code reader 411 and an RF tag reader 412.

The computer 400 has predetermined programs, for example, stored in the recording medium 410, and installs the programs stored in this recording medium 410 on the computer 400 via the external I/F 408 to make the predetermined programs executable.

The bus 409 is connected to the above elements, to transmit address signals, data signals, various control signals, and the like.

Note that the configuration in FIG. 4 is just an example. For example, the computer 400 may have the input device 406 and the display 407 externally, and the input device 406 and the display 407 may be a unified device including a display and an input device, for example, a touch panel display.

(Hardware Configuration of Wireless Tag)

Figure 5A:
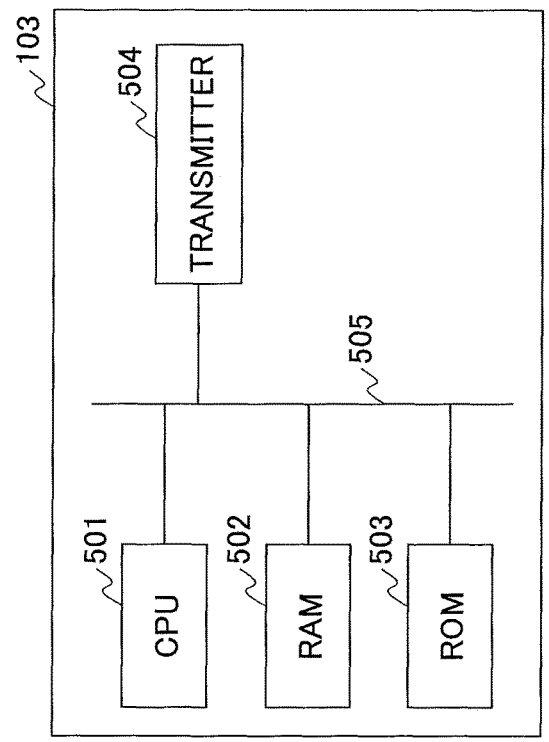
FIGS. 5A-5B are diagrams illustrating an example of a hardware configuration of a wireless tag according to an embodiment.
Figure 5B:
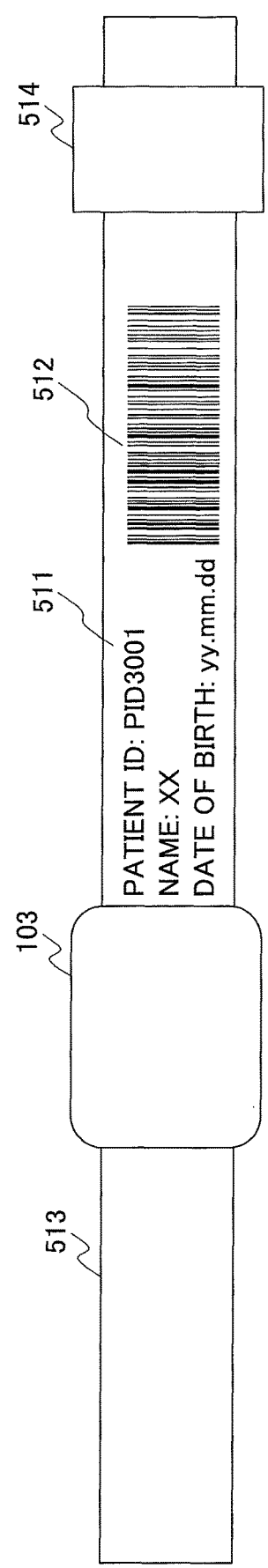

FIGS. 5A-5B are diagrams illustrating an example of a hardware configuration of the wireless tag 103 according to an embodiment.

FIG. 5A illustrates an example of a hardware configuration of the wireless tag 103. The wireless tag 103 includes, for example, a CPU 501, a RAM 502, a ROM 503, a transmitter 504, and a bus 505.

The CPU 501 is a processor to implement functions of the wireless tag 103, by executing a program stored in the ROM 503 or the like. The RAM 502 is a volatile memory that is used as a work area of the CPU 501. The ROM 503 is a non-volatile memory to store a program for the wireless tag 103, the wireless tag ID, and the like. The ROM 503 may be a rewritable non-volatile memory, for example, a flash ROM, an EEPROM (Electrically Erasable Programmable Read-Only Memory), or the like.

The transmitter 504 includes, for example, a transmitter circuit to transmit predetermined wireless signals of RFID or the like, and an antenna. An example of the predetermined wireless signal, a weak wireless signal in the 315-MHz band may be used. In this case, the predetermined wireless signal transmitted by the wireless tag 103 has a communicable distance (a reachable range) of, for example, about 10 m.

The bus 505 is connected to the above elements, to transmit address signals, data signals, various control signals, and the like.

FIG. 5B illustrates an example of a wrist band 513 to be attached to a wrist or the like of a patient to be admitted in the hospital 101. In the example in FIG. 5B, the wrist band 513 has information 511 about to identify the patient such as the patient ID, the name of the patient, and the date of birth, and a bar code 512 printed, to be attached to a wrist or the like of the patient to be admitted in the hospital 101, by using a catch 514. It is assumed that when the patient leaves the hospital 101, the wrist band 513 is, for example, cut off by scissors or the like, to be detached from the wrist or the like of the patient.

It is assumed that in the embodiment, the wireless tag 103 held by or attached to the patient is attached to the wrist band 513 so as not to be easily detached.

Also, it is desirable that a wireless tag 103 held by or attached to a person engaged in medical care, such as a doctor and a nurse, is built in a name plate, a badge, an identification card, a wrist band, a wearable terminal, or the like that is held by or attached to the person engaged in medical care.

Note that it is assumed that the wireless tag 103 transmits the tag ID stored in advance in the ROM 503 at predetermined time intervals (for example, every 30 seconds), by using the transmitter 504.

(Hardware Configuration of Detector)

Figure 6:
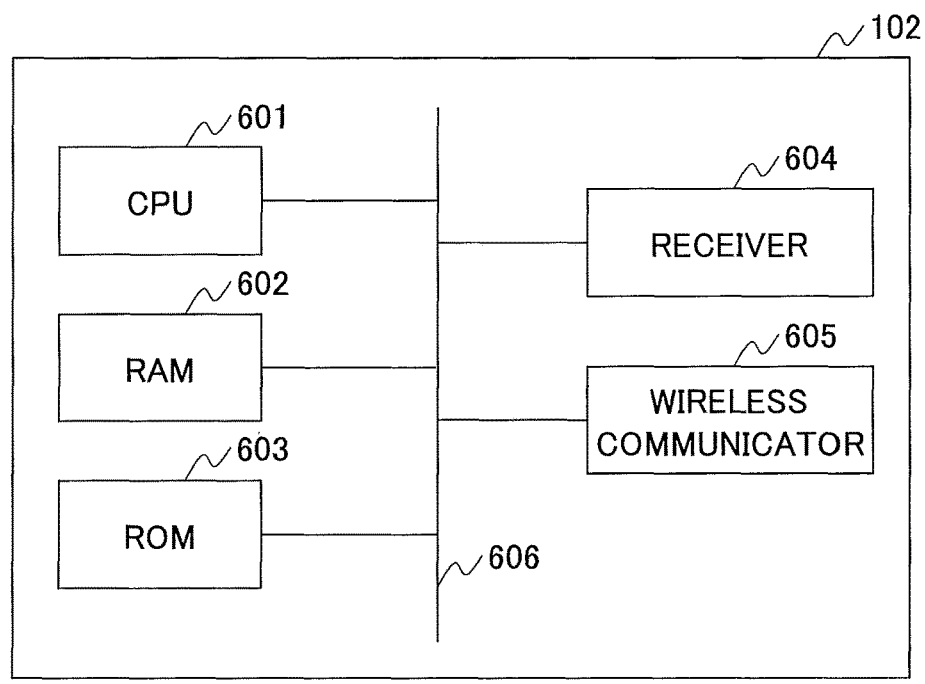
FIG. 6 is a diagram illustrating an example of a hardware configuration of a detector according to an embodiment.

FIG. 6 is a diagram illustrating an example of a hardware configuration of the detector 107 according to an embodiment. The detector 102 includes, for example, a CPU 601, a RAM 602, a ROM 603, a receiver 604, a wireless communicator 605, and a bus 606.

The CPU 601 is a processor to implement functions of the detector 102, by executing a program stored in the ROM 603 or the like. The RAM 602 is a volatile memory that is used as a work area of the CPU 601. The ROM 603 is a non-volatile memory to store a program for the detector 102, the detector ID, and the like. The ROM 603 may be a rewritable non-volatile memory, for example, a flash ROM, an EEPROM, or the like.

The receiver 604 includes, for example, a receiver circuit to receive a radio wave in a predetermined wireless protocol such as RFID, and an antenna.

The wireless communicator 605 includes, for example, a transceiver circuit to execute wireless communication with the gateway 105 by a wireless communication protocol different from the protocol used by the receiver 604, and an antenna. The wireless communicator 605 may communicate with the gateway 105 by using, for example, a wireless LAN, Zigbee (trademark), or a specific low-power wireless protocol in the 920-MHz band (IEEE802.15.4g).

The bus 606 is connected to the above elements, to transmit address signals, data signals, various control signals, and the like.

(Hardware Configuration of Gateway)

Figure 7:
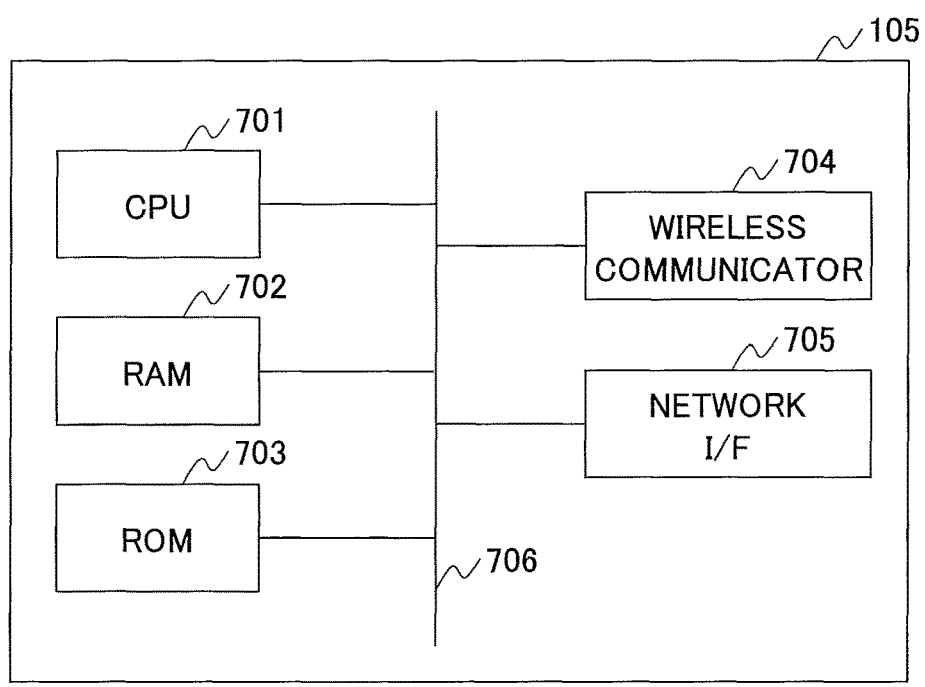
FIG. 7 is a diagram illustrating an example of a hardware configuration of a gateway according to an embodiment.

FIG. 7 is a diagram illustrating an example of a hardware configuration of the gateway 105 according to an embodiment. The gateway 105 includes, for example, a CPU 701, a RAM 702, a ROM 703, a wireless communicator 704, a network I/F 705, and a bus 706.

The CPU 701 is a processor to implement functions of the gateway 105, by executing a program stored in the ROM 703 or the like. The RAM 702 is a volatile memory that is used as a work area of the CPU 701. The ROM 703 is a non-volatile memory to store a program for the gateway 105 and the like. The ROM 703 may be a rewritable non-volatile memory, for example, a flash ROM, an EEPROM (Electrically Erasable Programmable Read-Only Memory), or the like.

The wireless communicator 704 includes, for example, a wireless circuit to execute wireless communication by the same wireless communication protocol as used by the wireless communicator 605 of the detector 102 described above, and an antenna.

For example, if using the specific low-power wireless protocol in the 920-MHz band, the wireless communicator 704 has the transmission speed around 200 Kbps, which is lower than the speed of other wireless protocols such as a wireless LAN and Zigbee, yet is capable of transmitting data at a consumed current around several dozen mA within a range up to several hundred meters.

It is assumed that a required number of the gateways 105 are installed to communicate with the detectors 102 on the floors in the hospital 101, depending on the wireless communication protocol of the wireless communicator 704.

The network I/F 705 is a communication interface to have the gateway 105 connect with a network such as the LAN 106.

The bus 706 is connected to the above elements, to transmit address signals, data signals, various control signals, and the like.

First Embodiment

<Functional Configuration>

Figure 8:
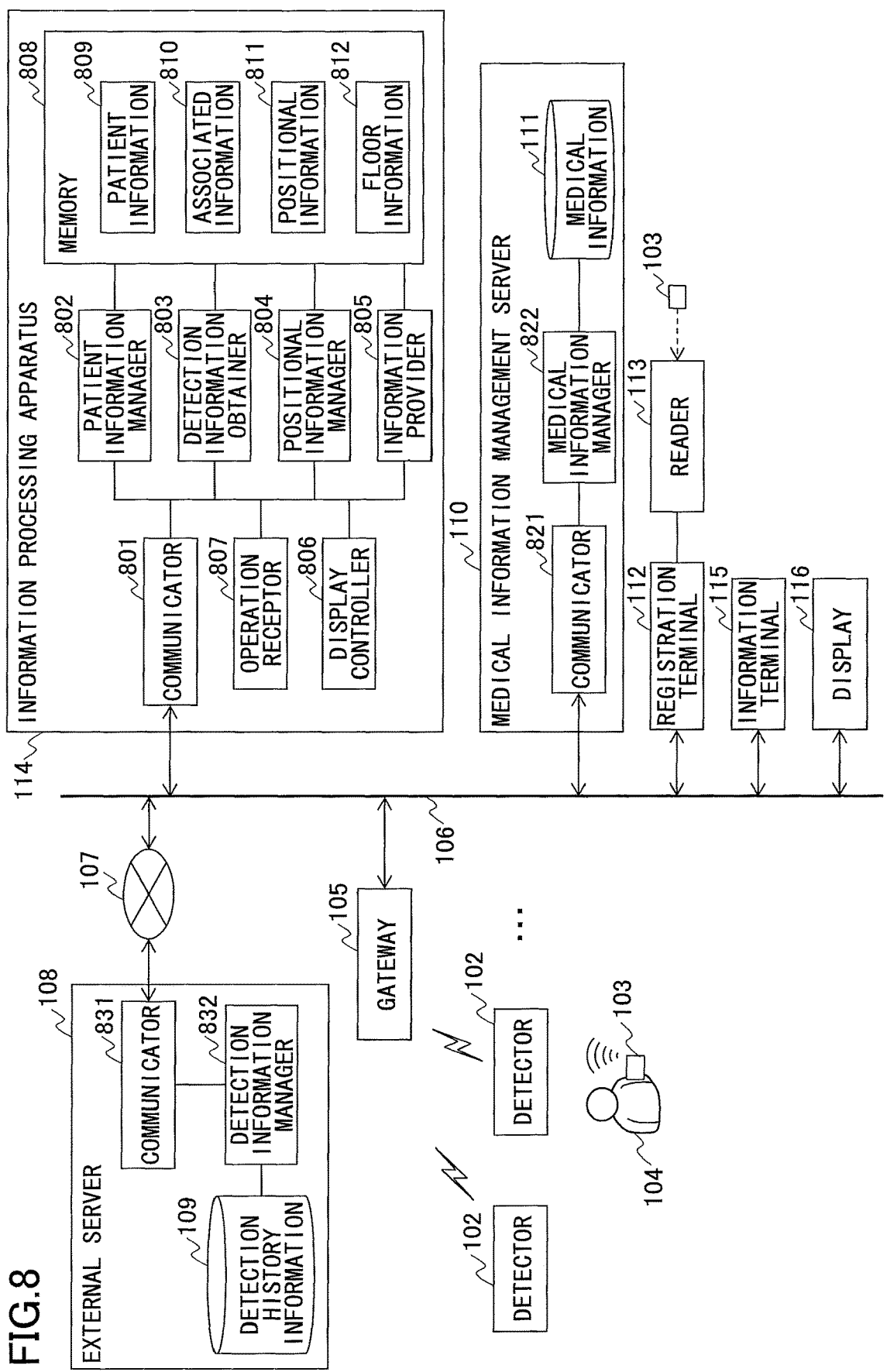
FIG. 8 is a functional configuration diagram of an information processing system according to a first embodiment.

FIG. 8 is a functional configuration diagram of the information processing system 100 according to a first embodiment.

(Functional Configuration of Information Processing Apparatus)

The information processing apparatus 114 includes a communicator 801, a patient information manager 802, a detection information obtainer 803, a positional information manager 804, an information provider 805, a display controller 806, an operation receptor 807, and a memory 808.

The communicator 801 has the information processing apparatus 114 connect with a network such as the LAN 106, to communicate with the external server 108, the medical information management server 110, the information terminal 115, the display 116, and the like. The communicator 801 is implemented, for example, by the network I/F 405 in FIG. 4 and a program that runs on the CPU 401 in FIG. 4.

The patient information management unit 802 (associating) associates the wireless tag ID of the wireless tag 103 attached to each patient in the hospital 101 with information about medical care of the patient (for example, the medical information 111), and manages the associated data. The patient information manager 802 is implemented, for example, by a program that runs on the CPU 401 in FIG. 4.

The patient information manager 802 stores in the memory 808, associated information 810 that has the wireless tag ID of the wireless tag 103 attached to the wrist band 513 attached to each patient, associated with identification information of the bar code 512 printed on the wrist band 513.

Based on this associated information 810, the patient information manager 802 associates identification information of the wireless tag 103 attached to the patient, with the medical information 111 managed by the medical information management server 110, and manages the associated data. For example, based on the associated information 810, the patient information manager 802 associates the medical information 111 obtained from the medical information management server 110, with the tag ID of the wireless tag 103, and stores and manages the associated data in the memory 808 as patient information 809.

Alternatively, the patient information manager 802 may use the wireless tag ID of the wireless tag 103, to obtain medical information about a patient having the wireless tag 103 attached, from the medical information management server 110, based on the associated information 810. Note that the associated information 810 and the patient information 809 will be described later.

The detection information obtainer 803 (obtaining) obtains the wireless tag ID of the wireless tag 103, the detector ID of the detector 102 that has detected the wireless tag ID, and the like in the hospital 101 from the external server 108. The detection information obtainer 803 is implemented, for example, by a program that runs on the CPU 401 in FIG. 4.

Note that the detector ID that the detection information obtainer 803 obtains from the external server 108 is an example of information about the detector 102. The information about the detector 102 may be, for example, positional information (for example, coordinates information) about the detector 102.

The positional information manager 804 (managing) uses information obtained by the detection information obtainer 803 (referred to as the "detection information", below), to manage information that represents the position of the wireless tag 103 attached to each patient in the hospital 101 (referred to as "positional information", below). The positional information manager 804 is implemented, for example, by a program that runs on the CPU 401 in FIG. 4.

For example, the positional information manager 804 stores in advance in the memory 808, floor information that is information about the floors in the hospital 101, as floor information 812. The floor information 812 includes, for example, the layout diagram 201 illustrated in FIGS. 2 and 3, and information about the detector IDs of the detectors 102 placed in the areas in FIG. 2 (the first to 31st areas, the E1 area, and the E2 area). The positional information manager 804 uses this floor information 812 and detection information obtained by the detection information obtainer 803, to manage positional information of the wireless tag 103 attached to each patient in the hospital 101, and stores the positional information, for example, in the memory 808 as positional information 811.

The information provider 805 (providing) uses positional information of the wireless tag 103 managed by the positional information manager 804, to provide various information items about medical care (medical information) of the patient having the wireless tag 103 attached. The information provider 805 is implemented, for example, by a program that runs on the CPU 401 in FIG. 4.

The information provider 805 provides (transmits) information to be provided, for example, as illustrated in FIG. 3, to the information terminal 115 or the display 116 connected via the LAN 106.

The display controller 806 displays various information items, for example, on the display 407 in FIG. 4, and is implemented, for example, by a program that runs on the CPU 401 in FIG. 4. For example, under control of the positional information manager 804 or the like, the display controller 806 displays a registration screen of the floor information 812 or the like on the display 407. Alternatively, the display controller 806 displays a registration screen of the associated information 810 or the like on the display 407, under control of the patient information manager 802. Further, the display controller 806 may display information to be provided by the information provider 805 on the display 407 or a display apparatus connected externally such as a projector.

The operation receptor 807 receives an input operation by a user, by using the input device 406 in FIG. 4, and is implemented, for example, by a program that runs on the CPU 401 in FIG. 4 or the like.

The memory 808 stores various information items including the patient information 809, the associated information 810, the positional information 811, and the floor information 812, and is implemented, for example, by the storage 404 and the RAM 402 in FIG. 4 and a program that runs on the CPU 401 in FIG. 4 or the like.

(Functional Configuration of External Server)

The external server 108 includes a communicator 831 and a detection information manager 832.

The communicator 831 has the external server 108 connect to a network such as the Internet 107, to communicate with the gateway 105, the information processing apparatus 114, and the like. The communicator 831 is implemented, for example, by the network I/F 405 in FIG. 4 and a program that runs on the CPU 401 in FIG. 4 or the like.

The detection information manager 832 receives the wireless tag IDs and the detectors ID indicated from the multiple detectors 102 via the gateway 105, and stores and manages the received IDs in the detection history information 109. Note that the detection history information 109 may be stored in, for example, the storage 404 of the external server 108, or may be stored in an external storage such as a storage server and a cloud service. Also, the detection history information 109 will be described later.

Also, in response to a request from the information processing apparatus 114 or the like, the detection information manager 832 provides at least a part of the detection history information 109 to the information processing apparatus 114 as the detection information. The detection information manager 832 is implemented, for example, by a program that runs on the CPU 401 in FIG. 4.

(Functional Configuration of Medical Information Management Server)

The medical information management server 110 includes a communicator 821 and a medical information manager 822.

The communicator 821 has the medical information management server 110 connect with a network such as the LAN 106, to communicate with the information processing apparatus 114, the registration terminal 112, and the like. The communicator 821 is implemented, for example, by the network I/F 405 in FIG. 4 and a program that runs on the CPU 401 in FIG. 4 or the like.

The medical information manager 822 stores and manages various information items about medical care registered and updated by the registration terminal 112 and the like as the medical information 111. The medical information 111 may be stored in, for example, the storage 404 of the medical information management server 110, or may be stored in a storage in the hospital 101 such as a storage server. Note that the medical information 111 will be described later.

Also, in response to a request from the information processing apparatus 114 and the like, the medical information manager 822 provides the medical information 111 to the information processing apparatus 114. The medical information manager 822 may output the medical information 111, for example, in a format readable by the information processing apparatus 114, such as CSV (Comma-Separated Values) format.

(Functional Configuration of the Others)

The registration terminal 112 uses, for example, the reader 113 and a built-in camera, to read the bar code 512 printed on a wrist band 513 attached to a patient hospitalized in the hospital 101. Also, the registration terminal 112 transmits various information items about medical care input on the registration terminal 112 along with the identification information of the read bar code 512 (referred to as the "bar code ID", below) to the medical information management server 110, to make a request for registration and update of the medical information.

The above function of the registration terminal 112 is implemented, for example, by a program for the registration terminal 112 that runs on the CPU 401 of the registration terminal 112 or the like.

For example, the information terminal 115 may display on the display 407 or the like, a menu for selecting information to be provided that is to be requested to the information processing apparatus 114, to obtain the information to be provided selected by the user from the information processing apparatus 114, and to display the obtained information to be provided on the display 407 or the like.

The above function of the information terminal 115 is implemented, for example, by a program for the information terminal 115 that runs on the CPU 401 of the information terminal 115 or the like.

The display 116 displays (or projects on a projection plane), for example, the information to be provided (image data) provided from the information processing apparatus 114 via a network such as the LAN 106.

<Example of Information Items>

Next, an example of information handled by the information processing system 100 will be described.

(Information Managed by External Server)

FIGS. 9A-9C are diagrams illustrating an example of information managed by an external server according to the first embodiment.

FIG. 9A illustrates an example of the detection history information 109 managed by the detection information manager 832. The detection history information 109 stores wireless tag IDs, each of which has the detector IDs of detectors 102 that have detected the wireless tag ID, and detected times when the wireless tag ID has been detected, associated.

Preferably, the detection history information 109 may include past detection history of wireless tag IDs. Various settings may be possible for a period during which the detection history is stored.

If the detection history is stored for 24 hours or longer, the detection history information 109 includes date information.

In the example in FIG. 9A, it can be seen that the wireless tag 103 having the wireless tag ID "TAG101001" has not moved out of an area corresponding to the detector ID "0005" (the fifth area in the example in FIG. 2). In this way, even if a new wireless tag ID is not detected, it is desirable that detection information is transmitted from the detectors 102 at predetermined time intervals (for example, every five minutes).

On the other hand, it can be seen that the wireless tag 103 having the wireless tag ID "TAG101003" has moved to an area corresponding to the detector ID "0026" at the time 9:33, and then moved to an area corresponding to the detector ID "0027" the time 9:34. In this way, if the detector 102 detects a new wireless tag ID, it is desirable that the detector 102 transmits the detection information each time it happens.

FIG. 9B illustrates an example of detection information provided by the external server 108 to the information processing apparatus 114. Detection information provided to the information processing apparatus 114 includes, for example, the latest detected time of the wireless tag ID of each of the multiple wireless tags 103 detected in the hospital 101, the detector ID of the detector 102 detected the wireless tag ID.

The information processing apparatus 114 can identify positions of the persons 104 having the respective wireless tags attached, by using this detection information and the floor information 812 stored in the memory 808. Note that even if information managed by the external server 108 is intercepted by a third person at the worst, the information only includes the wireless tags ID and the detectors ID, and hence, information about the medical care in the hospital 101 will not leak out.

FIG. 9C illustrates another example of positional information provided to the information processing apparatus 114 from the external server 108. In this way, the external server 108 can provide positional information that corresponds to specified date and time in response to a request from the information processing apparatus 114.

(Information Managed by Medical Information Management Server)

FIG. 10 is a diagram illustrating an example of the medical information 111 managed by the medical information management server 110 according to the first embodiment. In the example in FIG. 10, the medical information 111 includes records of a patient ID, a bar code ID, a name, a date of birth, a clinical department, condition information, planned data and time of a treatment, a place of the treatment, and chart information.

The "patient ID" represents identification information to identify a patient. The "bar code ID" represents identification information of the bar code 512 printed on the wrist band 513 that the patient has attached to a wrist or the like. The "name" represents the name of the patient. The "date of birth" represents the date of birth of the patient. The "clinical department" represents information about the clinical department that gives treatments to the patient.

The "condition information" represents conditions of the patient that may include various information items about the patient, for example, planned admission date, planned leaving date, information representing states of the disease, and information representing points to be cared. The "planned data and time of treatment" is information that represents planned date and time of a treatment for the patient. The "place of treatment" is information that represents a place where the patient receives the treatment. The "chart information" represents link information for referring to charts of the patient.

Note that the medical information 111 illustrated in FIG. 10 is just an example. The medical information 111 may include various information items about the medical care in this hospital 101.

(Information Managed by Information Processing Apparatus)

FIGS. 11A-12B are diagrams illustrating an example of information managed by the information processing apparatus 114 according to the first embodiment.

FIG. 11A illustrates an example of the associated information 810 managed by the patient information manager 802. In the example in FIG. 11A, the associated information 810 stores the wireless tag ID of the wireless tag 103 attached to each wrist band 513 illustrated in FIG. 5, and the bar code ID of the bar code 512 printed on the wrist band 513, associated with each other.

This associated information 810 may be provided, for example, by a manufacturer who manufactured the wrist bands 513, or may have been registered in advance by a person in charge using the registration terminal 112 or the like.

FIG. 11B illustrates an example of the patient information 809 managed by the patient information manager 802. The patient information 809 is information that has been stored in the memory 808 by the patient information manager 802 that has associated the wireless tag ID with the medical information 111 illustrated in FIG. 10, based on the associated information 810. By referring to this patient information 809, the information processing apparatus 114 can use various information items about medical care of the patient by using the wireless tag ID.

FIG. 12A illustrates an example of the floor information 812 managed by the positional information manager 804. The floor information 812 includes records of information items including, for example, a detector ID, a floor name, area information, room information, a floor map or a layout diagram, and placement information.

The "detector ID" represents identification information of a detector 102. The "floor name" represents information to identify a floor where the detector 102 is installed in the hospital 101. The "area information" represents information to identify an area where the detector 102 is installed on the floor where the detector 102 is installed.

The "room information" represents information that represents a room in which the detector 102 is installed on the floor where the detector 102 is installed. The "layout diagram" is image data that represents a placement of rooms on the floor where the detectors 102 are installed, for example, the layout diagram 201 as illustrated in FIGS. 2 and 3. In the example in FIG. 12A, the "layout diagram" stores link information to image data that represents the placement of the rooms on the floor.

The "placement information" is information that represents a placement of multiple areas that designate detection ranges 202 of multiple detectors 102, respectively, for example, as illustrated in FIG. 2. In the example in FIG. 12A, the "placement information" stores link information to information that represents the placement of the multiple area.

Note that the area information and the placement information may be, for example, coordinates information that represents positions at which the detectors 102 are installed, respectively.

In brief, the floor information 812 just stores the detectors ID of the respective detectors 102 installed in the hospital 101, each of which has information to identify the installed position of the detector 102 associated.

FIG. 12B illustrates an example of the positional information 811 managed by the positional information manager 804. The positional information 811 illustrated in FIG. 12B has been stored by the detection information obtainer 803 that has associated detection information illustrated in FIG. 9B obtained from the external server 108, with the floor information 812 illustrated in FIG. 12A.

By referring to this positional information 811, the positional information manager 804 can easily manage, for example, that a patient having a wireless tag 103 having the wireless tag ID "101000001" attached, is located in the fifth area (the private room A) at the time "9:45".

<Flow of Process>

Next, a flow of a process of a method for providing information by the information processing apparatus 114 will be described according to the embodiment.

(Process of Information Processing Apparatus)

FIG. 13 is a flowchart illustrating an overview of a process of the information processing apparatus 114 according to the first embodiment.

At Step S1301, the patient information manager 802 of the information processing apparatus 114 obtains the medical information 111 from the medical information management server 110 or the like.

At Step S1302, based on the associated information 810 stored in the memory 808, the patient information manager 802 associates the tag ID of the wireless tag 103 attached to the patient in the hospital 101, with the obtained medical information 111, and manages the associated data. For example, the patient information manager 802 generates the patient information 809 as illustrated in FIG. 11B, and stores and manages the information in the memory 808.

At Step S1303, the detection information obtainer 803 of the information processing apparatus 114 obtains detection information as illustrated in FIG. 9B from the external server 108.

At Step S1304, by using the detection information obtained at Step S1303, the positional information manager 804 of the information processing apparatus 114 manages positional information of the wireless tag 103 attached to the patient in the hospital 101. For example, the positional information manager 804 associates the detection information obtained at Step S1303, with the floor information 812 stored in the memory 808, to generate the positional information 811 as illustrated in FIG. 12B, stores the information in the memory 808, and manages the information.

At Step S1305, by using the positional information 811 managed by the positional information manager 804, the information provider 805 of the information processing apparatus 114 provides information about medical care of the patient having the wireless tag 103 attached (medical information). For example, the information provider 805 transmits information as illustrated in FIG. 3 to the information terminal 115, the display 116, and the like, to be displayed.

Next, a flow of a process by the information processing system 100 will be described.

(Process for Registration and Update of Medical Information)

FIG. 14 is a sequence chart illustrating an example of a process for registration and update of medical information according to the first embodiment.

For example, when a patient is to be admitted in the hospital 101, a person in charge of the admission has the reader 113 or the like execute a read operation of the bar code of a wrist band 513 of the patient. Thus, the registration terminal A 112a at the reception office for admission reads the bar code (the bar code ID) of the wrist band 513 (Step S1401).

Also, the person in charge of the admission inputs information about the patient, for example, the patient ID, the name, the date of birth, and the like, into the registration terminal A 112a. Thus, the registration terminal A 112a receives the input of the information about the patient (Step S1402).

Having received the input of the information about the patient, the registration terminal A 112a transmits a request for registration that includes the bar code ID read from the wrist band 513 and the information about the admitted patient, to the medical information management server 110 (Step S1403).

Having received the request for registration from the registration terminal A 112a, the medical information manager 822 of the medical information management server 110 associates the bar code ID included in the request for registration, with the information about the patient, and stores (registers) the associated data in the medical information 111 (Step S1404).

Steps S1401 to S1404 described above are executed, for example, for each patient to be admitted in the hospital 101.

Also, when the patient receives a treatment by a doctor after the admission in the hospital, the doctor giving the treatment has, for example, the reader 113 execute a read operation of the bar code of the wrist band 513 of the patient. Thus, the registration terminal B 112b for inputting information about treatment reads the bar code (the bar code ID) of the wrist band 513 of the patient (Step S1405).

Also, the doctor giving the treatment to the patient inputs information about the treatment including, for example, various information items about medical care of the patient into the registration terminal B 112b. Thus, the registration terminal B 112b receives the input of the information about medical care of the patient (Step S1406).

Having received the input of the information about the patient about treatment, the registration terminal B 112b transmits a request for update including the bar code ID read from the wrist band 513 of the patient, and the received information about medical care of the patient to the medical information management server 110 (Step S1407).

Having received the request for update from the registration terminal B 112b, the medical information manager 822 of the medical information management server 110 updates the information about treatment that corresponds to the bar code ID included in the request for update with the received information about the treatment.

Steps S1405 to S1408 described above are executed, for example, every time a doctor gives a treatment, and a nurse or the like gives medical care such as dosing.

The patient information manager 802 of the information processing apparatus 114 makes a request for obtaining medical information to the medical information management server 110, for example, at predetermined time intervals (for example, every three hours) (Step S1409).

Having received the request for obtaining medical information from the information processing apparatus 114, the medical information manager 822 of the medical information management server 110 transmits the medical information 111 to the information processing apparatus 114 as the request source (Step S1410).

Having received the medical information 111 from the medical information management server 110, the patient information manager 802 of the information processing apparatus 114 associates the wireless tag ID of the wireless tag 103, with the received medical information 111, stores and manages the associated data in the memory 808 as the patient information 809.

(Process for Obtaining Detection Information and Process for Providing Information)

Each of the wireless tags 103 attached to patients in the hospital 101 transmits the wireless tag ID of itself at predetermined time intervals (for example, every 30 seconds) (Step S1501).

Each of the detectors 102 installed in the hospital 101 transmits detected information to the external server 108 via the gateway 105 in response to detecting (receiving) a wireless tag ID transmitted from a wireless tag 103 (Steps S1502 and S1503). The information transmitted by the detector 102 at this moment includes the wireless tag ID detected by the detector 102 and the detector ID of the device itself.

Preferably, when detecting a new wireless tag ID, the detector 102 may transmit the detected wireless tag ID and the detector ID of the device itself to the external server 108. Also, when detecting a wireless tag ID that has been already detected, the detector 102 may transmit the detected wireless tag ID and the detector ID of the device itself to the external server 108 at predetermined time intervals (for example, every five minutes).

Having received the detection information transmitted from the detector 102, the detection information manager 832 of the external server 108 updates the detection history information 109 with the received information (Step S1504).

By continuously executing Steps S1501 to S1504 described above, the external server 108 accumulates and manages information relating to positions of the wireless tags 103 in the hospital 101 (the detection history information 109).

The detection information obtainer 803 of the information processing apparatus 114 transmits a request for obtaining detection information to the external server 108 at predetermined time intervals (for example, every minute) (Step S1505).

Having received a request for obtaining detection information from the information processing apparatus 114, the detection information manager 832 of the external server 108 transmits detection information, for example, as illustrated in FIG. 9B to the information processing apparatus 114 as the request source (Step S1506).

When the detection information obtainer 803 of the information processing apparatus 114 receives (obtains) the detection information from the external server 108, the positional information manager 804 of the information processing apparatus 114 updates the positional information 811 stored in the memory 808 by using the received detection information.

By continuously executing Steps S1505 to S1507 described above, the positional information 811 stored by the information processing apparatus 114 is updated at the predetermined time intervals.

A person engaged in medical care (for example, a doctor or a nurse) in the hospital 101 can use information provided by the information processing apparatus 114 by using the information terminal 115. For example, when an application compatible with the information processing system 100 is executed on the information terminal 115, a display information menu is displayed as illustrated in FIG. 16.

Figure 16:
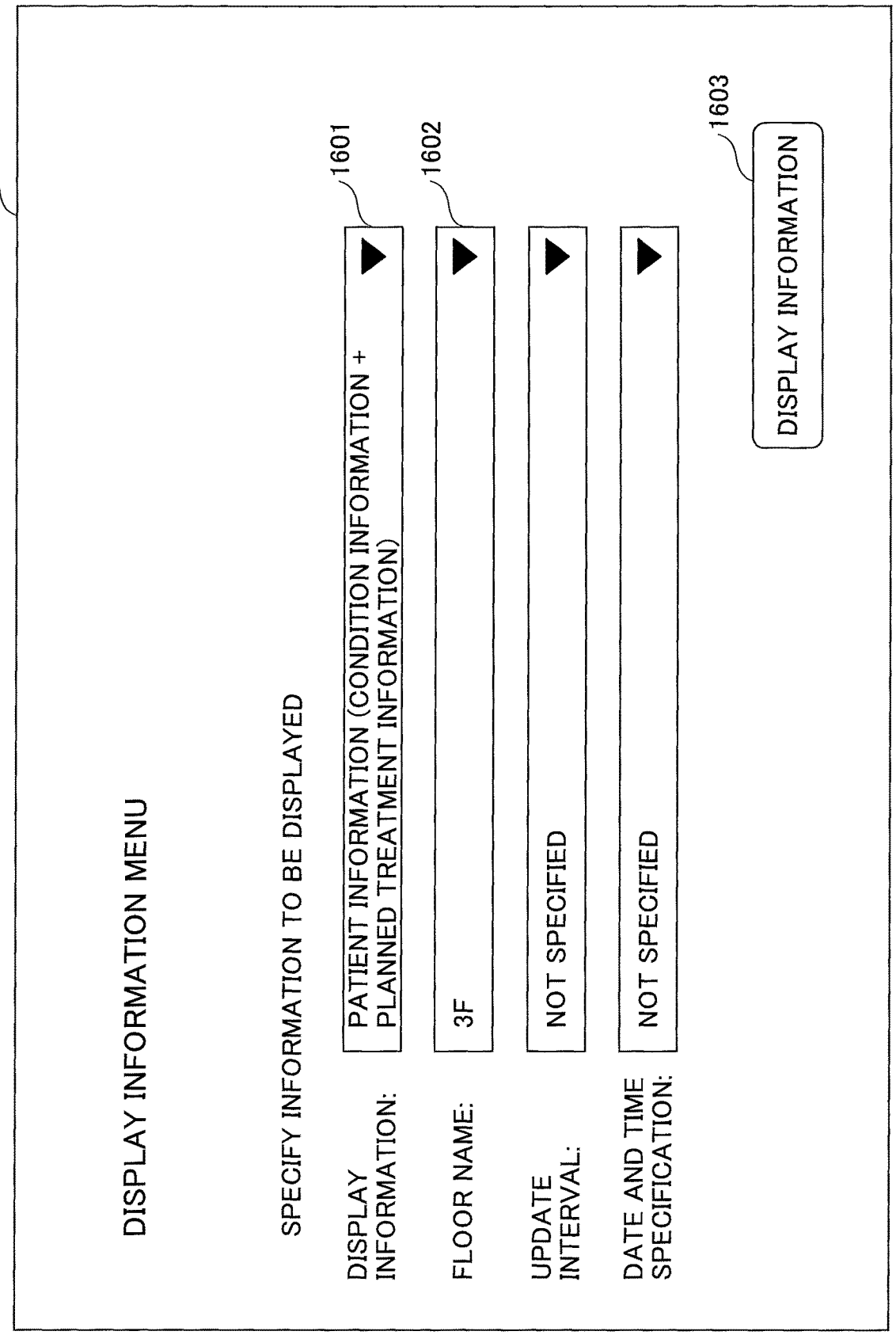
FIG. 16 is a diagram illustrating an example of a display screen on an information terminal according to the first embodiment.

FIG. 16 is a diagram illustrating an example of a display screen on the information terminal 100 according to the first embodiment. In the example in FIG. 16, the display screen 1600 on the information terminal 115 1600 includes a pull-down menu 1601 for selecting information to be displayed, a pull-down menu 1602 for selecting a floor name to be displayed, and a button 1603 for executing information display.

Preferably, the display screen 1600 on the information terminal 115 may include pull-down menus for specifying an update interval, date and time, and the like.

In the example in FIG. 16, "patient information (condition information+planned treatment information)" is selected as information to be displayed, and "3F (third floor)" is selected as the floor name. By selecting the button 1603, a person engaged in medical care may have information to be provided, for example, as illustrated in FIG. 3, displayed on the display 407.

Referring back to FIG. 15, description about the sequence chart will be continued.

Having received an input operation of information to be displayed on the display screen 1600, for example, as illustrated in FIG. 16 (Step S1508), the information terminal 115 transmits a request for obtaining the input information to the information processing apparatus 114 (Step S1509).

Having received the request for obtaining the information from the information terminal 115, the information provider 805 of the information processing apparatus 114 uses the positional information 811 and the patient information 809 stored in the memory 808, to generate information to be provided, for example, as illustrated in FIG. 3 (Step S1510). Also, the information provider 805 transmits the generated information to be provided to the information terminal 115 as the request source (Step S1511).

Preferably, the information provider 805 may update and transmit the information to be provided to the information terminal 115 at predetermined time intervals, by "update intervals" if specified on the display screen 1600, for example, as in FIG. 16, or default time intervals (for example, every minute) if not specified.

Having received the information to be provided from the information processing apparatus 114, the information terminal 115 displays the information to be provided (for example, the information as illustrated in FIG. 3) on the display 407.

In this way, it is possible for the information processing apparatus 114 according to the embodiment to provide positional information and medical information, by using the information processing apparatus 114 and the external server 108 while preventing the medical information from leaking out.

Thus, the information processing system 100 not only can manage where patients are in the hospital 101, but also can provide various medical information items, for example, where a patient having a specific condition is located, or where a patient supposed to receive a treatment next is located.

Second Embodiment

In a second embodiment, a case will be described in which an information processing apparatus 114 cooperates with a call manager that manages call information, for example, nurse calls, to provide information.

For example, if calls such as nurse calls are made at multiple places at the same time, there may be a case where a nurse or the like hesitates over determining which patient should be prioritized. Especially, if a call has been made in a shared space (for example, a toilet), it has been difficult by a conventional technology to determine the importance (emergency) of the call because the nurse does not know who is in toilet.

The information processing system 100 according to the second embodiment displays a place where a call has been made, along with the information about the patient at the place and the medical information about the patient, to make it easy to determine the importance (emergency) of the call.

<Functional Configuration>

Figure 17:
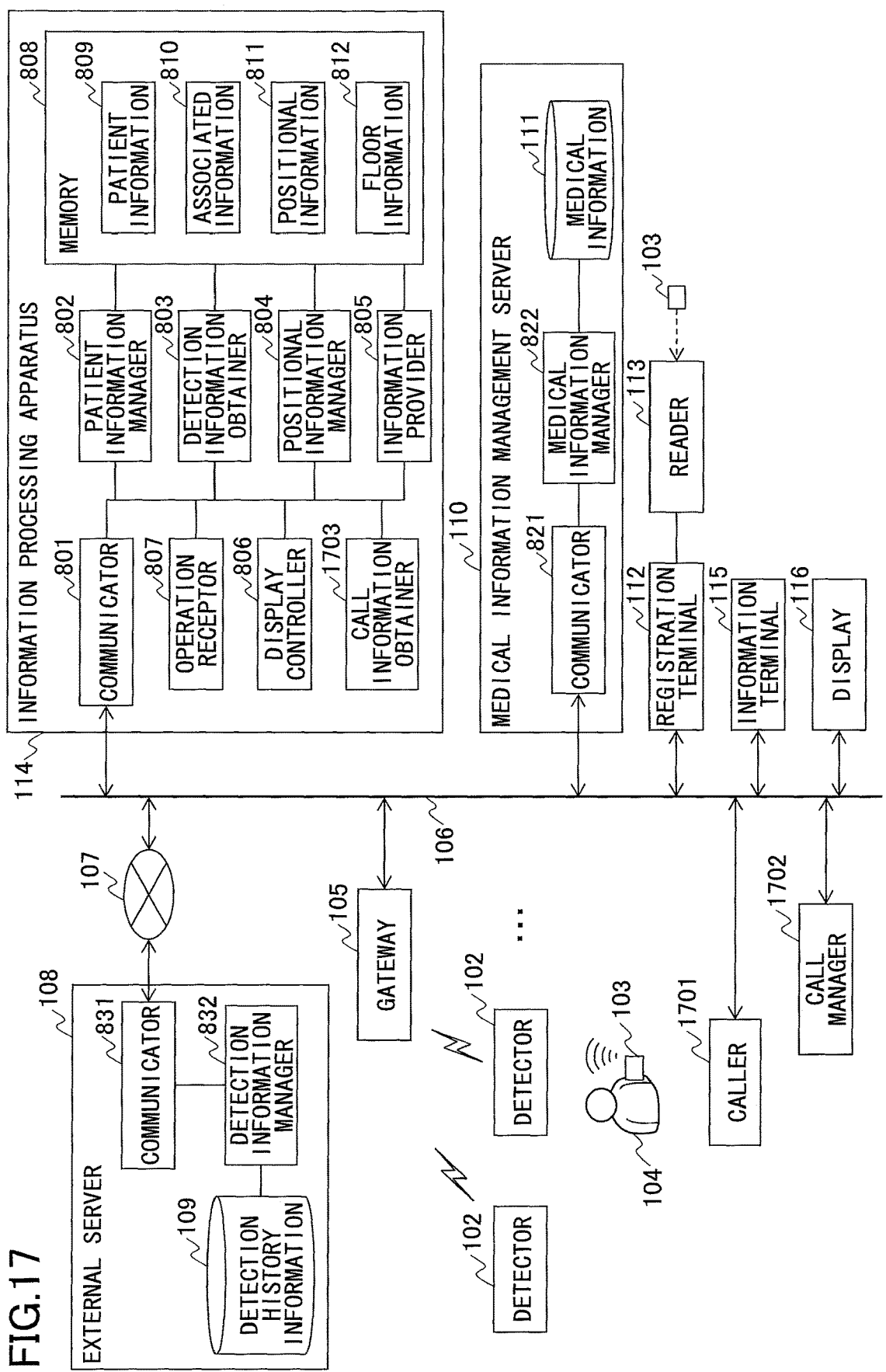
FIG. 17 is a functional configuration diagram of an information processing system according to a second embodiment.

FIG. 17 is a functional configuration diagram of an information processing system 100 according to the second embodiment. The information processing system 100 according to the second embodiment includes, in addition to the functional configuration of the information processing system 100 according to the first embodiment illustrated in FIG. 8, callers 1701, a call manager 1702, and a call information obtainer 1703. Note that the rest of the functional configuration is the same as the functional configuration of the information processing system 100 according to the first embodiment illustrated in FIG. 8, and hence, differences will be mainly described here.

The caller 1701 is an apparatus to call a nurse or the like, for example, by pressing a button, and disposed, for example, besides beds and toilets in the hospital 101. The call manager 1702 is an apparatus that displays, when the button of a caller 1701 is pressed, the position of the caller 1701 at which the button is pressed, on a display apparatus or the like, to indicate the call to a nurse or the like. Note that as the callers 1701 and the call manager 1702, an existing nurse call system or the like that has been already installed in the hospital 101 can be used.

Also, the information processing apparatus 114 according to the embodiment includes a call information obtainer 1703 (acquiring). The call information obtainer 1703 obtains call information from the callers 1701 or the call manager 1702, and to identify a place where a call has been made, and is implemented, for example, by a program that runs on the CPU 401 in FIG. 4.

Here, it is assumed in the following description that when a call has been made, the call information obtainer 1703 receives an indication of detection information of call that includes information about the place where the call has been made, from the call manager 1702.

<Flow of Process>

Figure 18:
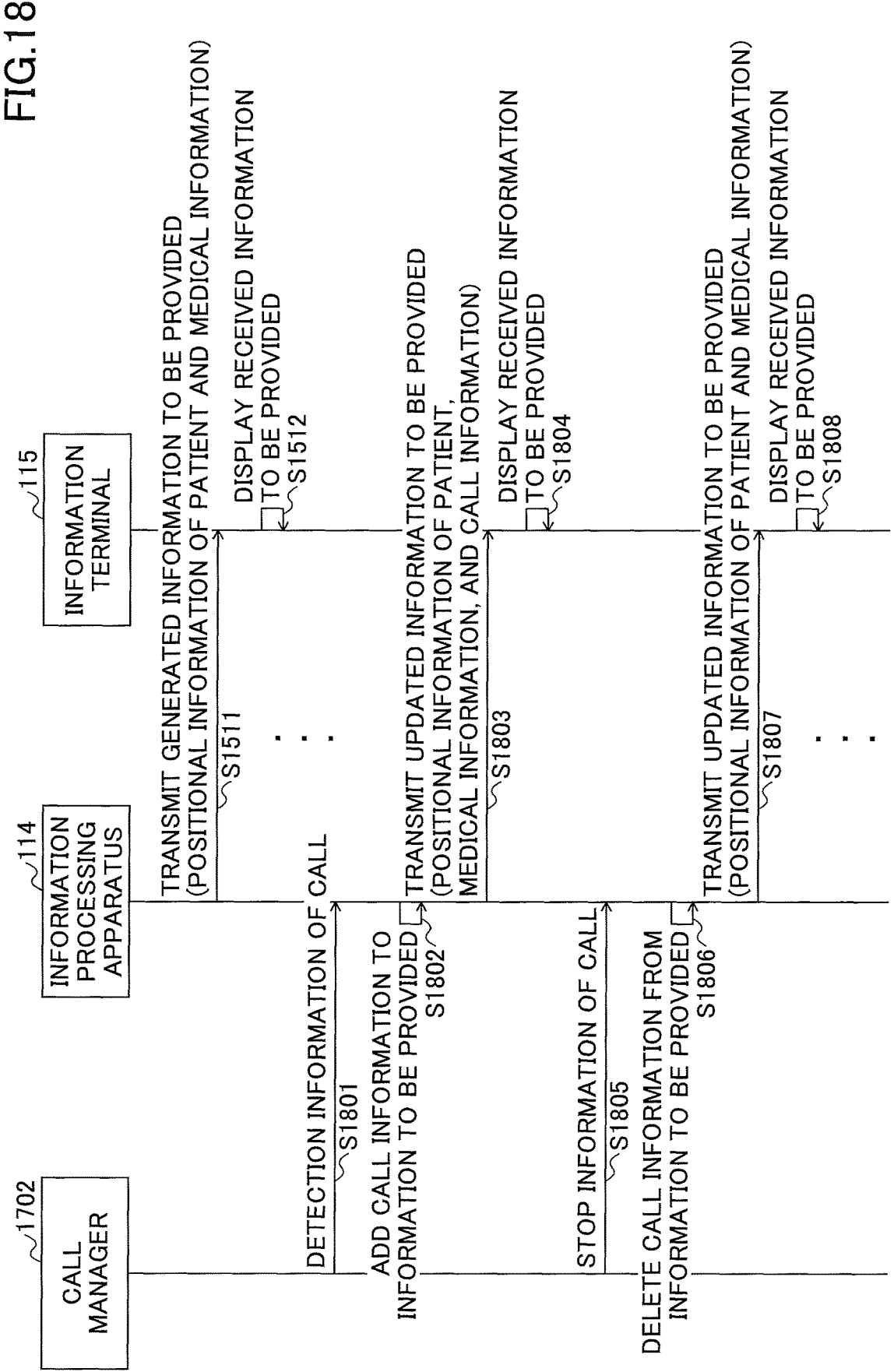
FIG. 18 is a sequence chart illustrating an example of a process for providing information according to the second embodiment.

FIG. 18 is a sequence chart illustrating an example of a process for providing information according to the second embodiment. At the beginning in FIG. 18, it is assumed that the information processing apparatus 114 has transmitted information to be provided to the information terminal 115 at the predetermined time intervals, for example, by the process for providing information illustrated in FIG. 15 (Steps S1511 and S1512).

Having detected that a call has been made by the caller 1701, the call manager 1702 indicates detect information representing that the call has been detected, to the information processing apparatus 114 (Step S1801). It is assumed that this detection information of the call includes information that represents the place where the call has been made (for example, the room information or the like). Also, the call information obtainer 1703 of the information processing apparatus 114 having received the detection information of the call from the call manager 1702 indicates to the information provider 805 information representing that the call has been made, and the information about the place where the call has been made, based on the received detection information of call.

The information provider 805 having received the indication adds the call information to the information to be provided that has been indicated to the information terminal 115 at Step S1511 in FIG. 18, to update the information to be provided (Step S1802). Also, the information provider 805 transmits the updated information to be provided to the information terminal 115 (Step S1803).

Figure 19:
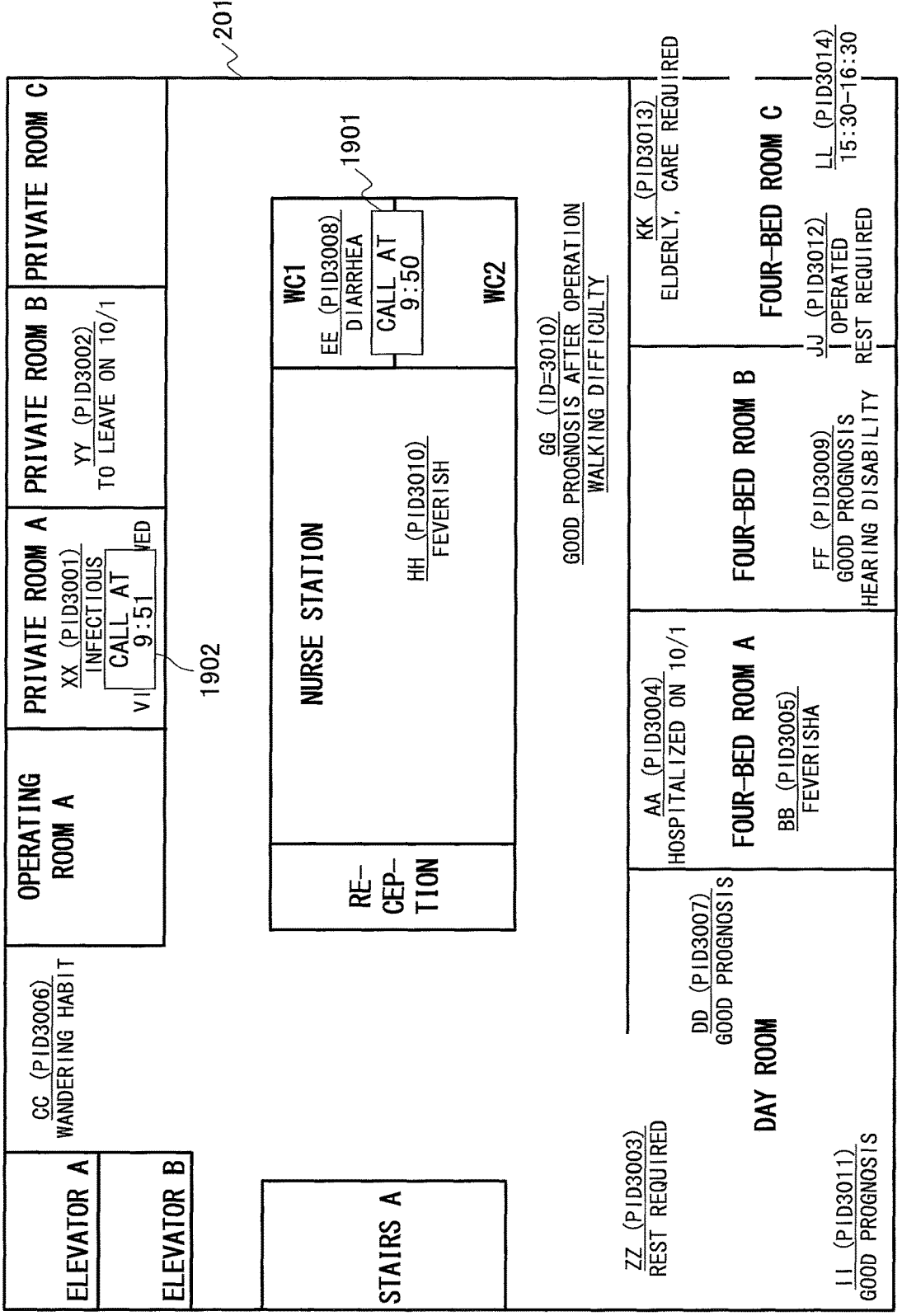
FIG. 19 is a diagram illustrating an example of information provided by an information processing apparatus according to the second embodiment.

The information terminal 115 displays the information to be provided indicated from the information processing apparatus 114 on the display 407 (Step S1804). FIG. 19 illustrates an example of a display screen displayed on the display 407 of the information terminal 115 at this moment.

FIG. 19 is a diagram illustrating an example of information provided by the information processing apparatus 114 according to the second embodiment. In the example in FIG. 19, the information provided by the information provider 805 of the information processing apparatus 114 and to be displayed includes, in addition to the information items described in FIG. 3, information items 1901 and 1902 that represent places where calls have been made, respectively.

Preferably, the information items 1901 and 1902 that represent the places where the calls have been made may include information about the time when the calls have been made, respectively.

The example in FIG. 19 displays that one of the calls has been made at 9:50 in WC1, a patient EE (having the patient ID "PID3008") is located in WC1, and the patient EE is in a condition of "diarrhea".

In this way, when a call has been made in a shared space other than a bed of a patient, the information processing system 100 according to the embodiment makes it easy to determine the patient located at the place, and information that represents the condition of the patient.

Also, the example in FIG. 19 displays information that the other call has been made at 9:51 in the private room A, the patient XX (having the patient ID "PID3001") is located in the private room A, and the patient XX has the conditions of "infectious disease" and "no visitors allowed".

In this way, according to the embodiment, if a call has been made in the hospital 101, information that represents the condition of the patient who has made the call is provided. Therefore, a nurse or the like can easily determine the importance, the emergency, and the like of the call.

Referring back to FIG. 18, description about the sequence chart will be continued.

When detecting that the caller 1701 has stopped the call, the call manager 1702 indicates "stop information of call" representing that the call has been stopped to the information processing apparatus 114 (Step S1805). It is assumed that this stop information of call includes information that represents a place at which the call has been stopped (for example, room information or the like). Also, having received the stop information of the call from the call manager 1702, the call information obtainer 1703 of the information processing apparatus 114 indicates that the call has been stopped, and information that represents the place where the call has been stopped, to the information provider 805, based on the received stop information of the call.

Having received the indication, the information provider 805 deletes the call information of the call that has been stopped from the information to be provided (Step S1806). Also, the information provider 805 transmits the updated information to be provided to the information terminal 115 (Step S1807).

The information terminal 115 displays the information to be provided indicated from the information processing apparatus 114 on the display 407 (Step S1808).

In this way, the information processing system 100 according to the embodiment provides call information in addition to information to be provided as provided in the first embodiment.

Thus, the information processing system 100 according to the embodiment makes it easy for the user to determine the importance (emergency) of a call because the system displays the place where the call has been made, as well as the information about the patient located at the place, and the medical information about the patient.

Third Embodiment

In a third embodiment, an example of a case will be described in which an information processing system 100 provides information about a patient, persons engaged in medical care (a doctor, a nurse, and the like), drugs, and the like at a place where medical care such as a treatment and a dosing are to be given.

FIGS. 20A-20B are diagrams illustrating an example of information managed by an information processing apparatus 114 according to the third embodiment.

In associated information 810 illustrated in FIG. 20A, in addition to the associated information 810 according to the first embodiment illustrated in FIG. 11A, information items "doctor ID", "nurse ID", "drug ID", and the like are associated with a wireless tag ID, and stored.

The "doctor ID" represents identification information to identify a doctor in the hospital 101. The "nurse ID" represents identification information to identify a nurse or the like in the hospital 101. The "drug ID" represents identification information to identify a drug in the hospital 101. Note that a doctor and a nurse are examples of a person engaged in medical care who gives medical care.

Patient information 809 illustrated in FIG. 20B includes information about each patient in the hospital 101, information about time and place where a medical care is to be given the patient, information about a person engaged in medical care who gives the medical care, and information about a drug to be used in the medical care, which are associated with the wireless tag ID of the wireless tag 103 attached to the patient.

In FIG. 20B, a patient ID, a bar code ID, a name of a patient are examples of information about the patient. A medical practitioner ID, a wireless tag ID of a medical practitioner are examples of information about a person engaged in medical care. An administered drug ID and the wireless tag ID of the drug are examples of information about a drug.

Note that an information item in parentheses under the "planned place of treatment" of the patient information 809 illustrated in FIG. 20B, represents the detector ID of a detector 102 installed at a planned place of the treatment. In this way, information about the "planned place of treatment" may include the detector ID of a detector 102 installed at a planned place of the treatment.

In this way, in the embodiment, the patient information manager 802 of the information processing apparatus 114 manages the wireless tag ID of a wireless tag 103 attached to a person engaged in medical care who gives a medical care to a patient in the hospital 101.

Preferably, the patient information manager 802 may manage the wireless tag ID of a wireless tag 103 attached to a drug to be used in the medical care of the patient in the hospital 101.

<Example of Information to be Provided>

FIGS. 21A-21D are diagrams illustrating examples of display screens on the information terminal 115 according to the third embodiment.

FIG. 21A illustrates an example of a display screen 2101 on the information terminal 115 according to the embodiment. In the example in FIG. 21A, the display screen 2101 includes a pull-down menu 2111 for selecting "room information", a pull-down menu 2112 for selecting "display information", a pull-down menu 2113 for giving "date and time specification", and a button 2114 to display the information.

A user of the information terminal 115 (for example, a nurse) may use the pull-down menu 2111 for selecting the "room information", to specify a place at which relevant information needs to be displayed (for example, a place where a medical care is to be given).

Also, the user may use the pull-down menu 2112 for selecting the "display information", to select a type of display information to be displayed. The type of display information includes, for example, matching information about a patient, matching information about a person engaged in medical care, matching information about a drug, and information about three-point dosing confirmation, which will be described later.

Further, the user may use the pull-down menu 2113 for giving the "date and time specification", to specify the date and time to be displayed. Although a current time is usually specified as the date and time, past date and time may be specified, to confirm a past medical care has been given properly. Here, it is assumed that a current time is specified in the following description.

After having used the pull-down menus to specify the display information to be displayed, the user selects the button 2114 to display the information. This makes the information terminal 115 obtain required information from the information processing apparatus 114, and based on the obtained information, display a display screen 2102, for example, as illustrated in FIG. 21B, on the display 407.

In the example in FIG. 21B, patient matching information is displayed as the display information. The patient matching information represents whether a patient located at a specified place (for example, a place where a medical care is to be given) is actually the patient to be treated. The patient matching information includes, for example, as illustrated in FIG. 21B, a room name, date and time, the wireless tag ID of the patient to be treated, the wireless tag ID of the patient in the private room A, and a determination result "OK".

The "wireless tag ID of the patient to be treated" corresponds to, for example, the wireless tag ID of the patient in FIG. 20B. Also, the "wireless tag ID of the patient in the private room A" is the wireless tag ID of the wireless tag 103 attached to the patient who has been determined located in the private room A by the positional information managed by the positional information manager 804 of the information processing apparatus 114.

If these two wireless tag IDs match, the patient located in the private room A can be determined as the patient to be treated as stored in the patient information 809, and an "OK" is displayed as the determination result.

On the other hand, if the "wireless tag ID of the patient to be treated" and the "wireless tag ID of the patient in the private room A" do not match, an "NG" is displayed as the determination result.

Note that in the embodiment, it is not mandatory that the positional information manager 804 generates the positional information 811 as illustrated in FIG. 11B. For example, the positional information manager 804 may manage positional information of a wireless tag 103 by using detection information as illustrated in FIG. 9B that has been obtained from the external server 108 by the detection information obtainer 803.

In this case, for example, as illustrated in FIG. 20B, the detector ID of the detector 102 installed at the planned place for the medical care may be stored in the "planned place of treatment" or the like of the patient information 809.

By using the patient information 809, for example, as illustrated in FIG. 20B, the information provider 805 can identify the detector ID "00005" installed in the "private room A", and the wireless tag ID of the patient "101000001" to be treated.

The information provider 805 can also identify the wireless tag ID of the patient located in the area (the private room A) where the detector ID "00005" is installed, by the detection information obtained by the detection information obtainer 803 from the external server 108.

Thus, the information provider 805 can provide the "wireless tag ID of the patient to be treated" and the "wireless tag ID of the patient in the private room A" to the information terminal 115 or the like.

<Flow of Process>

FIG. 22 is a sequence chart illustrating an example of a process of an information processing system 100 according to the third embodiment. Here, an example of a case will be described in which "information about three-point dosing confirmation" is to be displayed as the display information.

The three-point dosing confirmation is, for example, work to confirm whether three points about dosing a drug to a patient are correct, in terms of the patient to be given the dosing, the person engaged in medical care who gives the dosing (for example, a nurse), and the drug to be dosed. This work has been conventionally done by using, for example, a bar code and the like.

A user of the information terminal 115 (for example, a nurse dosing a drug) inputs the room information on the display screen 2103 of the information terminal 115, for example, as illustrated in FIG. 21C, selects the "information about three-point dosing confirmation" as the display information, and selects the button "display information". Thus, the information terminal 115 receives the input of information to be displayed (Step S2201).

The information terminal 115 having received the input of information to be displayed, transmits a request for obtaining information to the information processing apparatus 114 (Step S2202). This request for obtaining information includes the information received as input at Step S2201, namely, "private room A" as the room information, "information about three-point dosing confirmation" as the display information, and "current time" as date and time specification.

Having received the request for obtaining the information described above from the information terminal 115, the information provider 805 of the information processing apparatus 114 transmits (provides), for example, information required for executing the three-point dosing confirmation to the information terminal 115 (Step 2203).

The information transmitted at this moment includes, for example, the "wireless tag ID of patient" to whom the dosing is planned at the current time in the room A, the "wireless tag ID of the medical practitioner", the "wireless tag ID of the drug", and the "wireless tag ID of wireless the tag in the private room A" managed by the positional information manager 804.

In this case, the information terminal 115 can determine the matching by comparing the "wireless tag ID of patient", the "wireless tag ID of medical practitioner", and the "wireless tag ID of drug" received from the information processing apparatus 114, with the corresponding "wireless tag IDs of wireless the tags in the private room A", respectively.

Also, as another example, the information provider 805 may determine the matching of the patient, the person in charge of the medical care, and the drug, by using the information items described above, to transmit a determined result to the information terminal 115.

In brief, the information provider 805 of the information processing apparatus 114 just needs to provide information required for determining the matching of the three-point dosing confirmation for the information terminal 115.

Having received the information for the three-point dosing confirmation from the information processing apparatus 114, the information terminal 115 determines the matching of the patient, the person in charge of the medical care, and the drug based on the received information (Step S2204), and displays a display screen that indicates a determination result (Step S2205). FIG. 21D illustrates an example of the display screen for the information about three-point dosing confirmation displayed at this moment.

In the example in FIG. 21D, the display screen 2104 of the information about three-point dosing confirmation designates that whether the matching is confirmed for the wireless tag IDs of the patient, the person in charge of the medical care, and the drug, respectively, and a determination result. Note that if all of the wireless tag IDs of the patient, the person in charge of the medical care, and the drug match, respectively, the determination result is "OK". On the other hand, if any one of the wireless tag IDs of the patient, the person in charge of the medical care, and the drug does not match, the determination result is "NG".

If receiving a request for the "patient matching information" from the information terminal 115, the information provider 805 of the information processing apparatus 114 provides information for determining whether a patient located at a place where a medical care is to be given is actually the patient to whom the medical care is to be given at the place.

Also, if receiving a request for the "matching information about the person in charge of medical care" from the information terminal 115, the information provider 805 provides information for determining whether a person in charge of medical care located at a place where a medical care is to be given, is actually the person in charge of the medical care who is supposed to give the medical care at the place.

Further, if receiving a request for the "drug matching information" from the information terminal 115, the information provider 805 provides information for determining whether a drug located at a place where a medical care is to be given, is actually the drug supposed to be used in the medical care at the place.

Furthermore, if receiving a request for "information about three-point dosing confirmation" from the information terminal 115, the information provider 805 provides information for determining matching of a patient at a place where a medical care is to be given, a person in charge of the medical care, and a drug.

Note that display screens as illustrated in FIGS. 21B and 21D may be generated by the information provider 805 of the information processing apparatus 114, to be displayed on the information terminal 115 and the display 116.

Fourth Embodiment

In a fourth embodiment, as an example more specific than in the third embodiment, an example of a case will be described in which matching is determined for a patient, a doctor, a nurse, a drug, a device (a medical device or the like,), and the like, that are located at a place where an operation is to be performed in the hospital 101.

FIG. 23 is a diagram illustrating an example of associated information according to the fourth embodiment. Associated information 810 illustrated in FIG. 23 includes information about "device ID" and the like in addition to the associated information according to the third embodiment illustrated in FIGS. 20A-20B. The "device ID" represents the wireless tag ID of a wireless tag 103 attached to one of various devices to be used for medical care in the hospital 101.

FIG. 24 is a diagram illustrating an example of patient information according to the fourth embodiment. Patient information 809 illustrated in FIG. 24 includes, in addition to the patient information in the third embodiment illustrated in FIGS. 20A-20B, an operation ID, an operating room, planned date and time of an operation, a device ID, and the wireless tag ID of the device. Note that the patient information 809 according to the embodiment may further include information about a drug ID and a wireless tag ID of the drug as illustrated in FIGS. 20A-20B.

Information items such as the operation ID, the operating room, the planned date, and the planned date and time of the operation constitute information about a planned operation, which is an example of information about medical care performed in the hospital 101.

<Example of Information to be Provided>

Figure 25A:
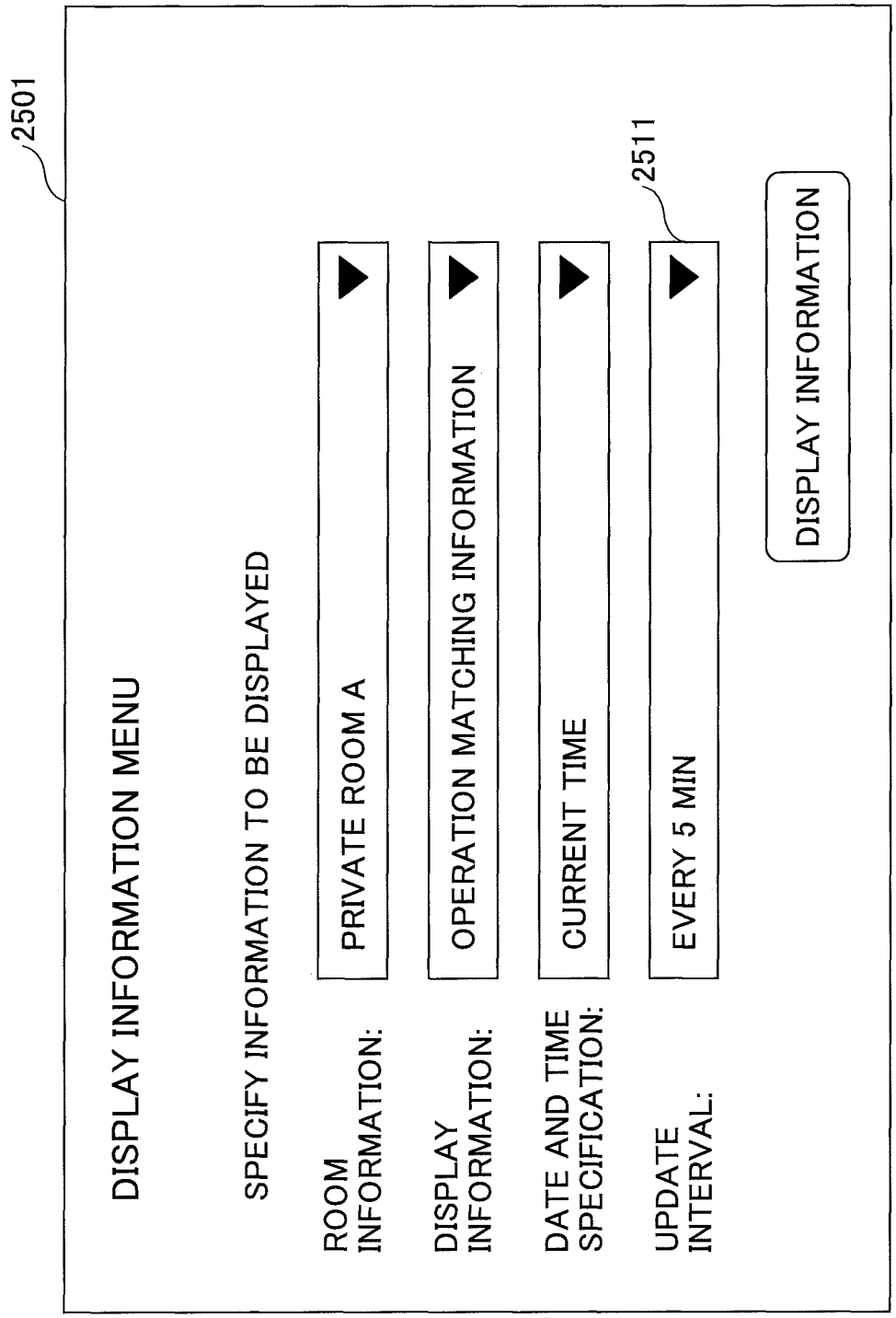

FIGS. 25A-25C are diagrams illustrating examples of display screens on an information terminal 115 according to the fourth embodiment.

FIG. 25A illustrates an example of a display screen 2501 on the information terminal 115 according to the embodiment. In the example in FIG. 25A, the display screen 2501 includes, as in the third embodiment, pull-down menus for selecting "room information", "display information", and "date and time specification", respectively, and a button to display the information.

The display screen 2501 according to the embodiment also includes a pull-down menu 2511 for selecting an update interval of the display information. In the embodiment, the information provider 805 of the information processing apparatus 114 transmits the information to be provided to the information terminal 115 at specified update intervals, to have the information terminal 115 update the display information. Compared to medical practice such as dosing and treatment, it is often the case that an operation takes a longer time, and is performed by a lot more persons engaged medical care, with various medical devices. Therefore, it is assumed here to continuously provide information for matching about an operation.

A user uses the pull-down menus, specifies the display information to be displayed, and selects the button to display the information, for example, to have a display screen 2502 displayed as illustrated in FIG. 25B.

FIG. 25B illustrates an example of a display screen 2502 about operation matching information. This display screen 2502 indicates, for example, a room name; date and time; information that represents whether matching has been confirmed for a wireless tag ID of a patient, the wireless tag ID of a doctor, the wireless tag ID of a nurse, and the wireless tag ID of a device; and a determination result. Also, this display screen 2502 is continuously updated at the specified update intervals (for example, every five minutes) until, for example, the end button is selected.

FIG. 25C illustrates an example of a display screen 2503 about updated operation matching information. The example in FIG. 25C indicates that the wireless tag ID of the nurse does not match, and accordingly, the determination result does not match.

In this way, the information processing system 100 according to the embodiment continuously updates and provides information that represents the matching about an operation (an example of medical care) based on positional information about wireless tags of a patient, a doctor, a nurse, a device, and the like.

Thus, the information processing system 100 can continuously provide new operation matching information timely even if a doctor, a nurse, a device or the like is changed, for example, during an operation.

Fifth Embodiment

In a fifth embodiment, an example of a case will be described in which an information processing apparatus 114 provides information to be provided for past date and time.

FIG. 26 is a diagram illustrating an example of a display screen on an information terminal 115 according to the fifth embodiment. A display screen 2600 on the information terminal 115 illustrated in FIG. 26 represents an example of a case in which past date and time is specified as "date and time specification" on the display screen 1600 according to the first embodiment illustrated in FIG. 16.

It is desirable that items displayed to be selected in the pull-down menu of the date and time specification on the display screen 2600, only include dates and times that can be displayed by the information processing system 100.

<Flow of Process>

FIG. 27 is a sequence chart illustrating an example of a process of an information processing system 100 according to the fifth embodiment.

For example, if a user of the information terminal 115 selects the button "display information" on the display screen 2600 illustrated in FIG. 26, the information terminal 115 receives the input of information to be displayed (Step S2701).

If receiving input of information to be displayed in which past date and time is specified, the information processing apparatus 114, the information terminal 115 transmits a request for obtaining information for the specified past date and time (Step S2702).

Having received the request for obtaining information for the specified past date and time, the detection information obtainer 803 of the information processing apparatus 114 transmits a request for obtaining detection information for the specified past date and time to the external server 108 (Step S2703).

Having received the request for obtaining the detection information, the external server 108 transmits the detection information for the specified past date and time to the information processing apparatus 114 (Step S2704).

Having received the detection information from the external server 108, the positional information manager 804 of the information processing apparatus 114 generates positional information 811 at the past date and time (Step S2705).

Also, the patient information manager 802 of the information processing apparatus 114 transmits a request for obtaining medical information for the specified past date and time to the medical information management server 110 (Step S2706).

Having received the request for obtaining the medical information, the medical information management server 110 transmits the medical information for the specified past date and time to the information processing apparatus 114 (Step S2707).

Having received the medical information from the medical information management server 110, the patient information manager 802 of the information processing apparatus 114 generates patient information 809 at the past date and time (Step S2708).

The information provider 805 of the information processing apparatus 114 generates information to be provided for the past date and time (Step S2709), and transmits the generated information to be provided to the information terminal 115 (Step S2710).

Having received the information to be provided from the information processing apparatus 114, the information terminal 115 displays the received information to be provided on the display 407 or the like.

By using positional information of the wireless tag 103 attached to the patient on past date and time, for example, as in the above steps, the information processing system 100 can provide the medical information about the patient.

Other Embodiments

System configurations of the information processing system 100 described in the above embodiments are just examples, and the information processing system 100 may have various system configurations other than the above.

For example, the medical information management server 110 that manages the medical information 111 may be separated into multiple server apparatuses that manage multiple medical information items (for example, inpatient information, chart information, and dosing information), respectively.

Also, the information processing apparatus 114 may include the medical information manager 822 that manages at least a part of the medical information 111.

Further, although a case has been described for the associated information 810 illustrated in FIG. 11A in which the wireless tag ID is different from the bar code ID, the wireless tag 103 may transmit the same ID as the bar code ID.

Furthermore, a case has been described with FIG. 14 in which when a patient is to be admitted, the person in charge at the reception office for admission reads the bar code ID from the wrist band 513, but the person in charge at the reception office for admission may read the wireless tag ID from the wrist band 513.

Alternatively, the patient information manager 802 of the information processing apparatus 114 may associate the wireless tag ID with the patient ID printed on the wrist band 513, to be managed as the associated information 810. In this case, the patient information manager 802 may associate the wireless tag ID with the medical information 111 of the patient, to manage the patient information 809, based on the patient ID.

Also, the above embodiments have been described with the hospital 101 as an example, the present disclosure can be applied to not only a hospital but also various facilities including, for example, an elderly care facility and a public health center.

For example, the information processing apparatus 114 associates the wireless tag ID of the wireless tag 103 attached to each patient in the hospital 101 or another facility with the medical information about the patient, manages the associated data, and uses positional information of the wireless tag 103 to provide various medical information items of the patient.

Also, the information processing apparatus 114 manages positional information of the wireless tag 103 attached to the patient by using detection information provided from the external server 108 that manages detection information of the wireless tag 103, and hence, the cost relating to management of the positional information can be reduced.

Further, since information handle by the external server 108 is restricted to wireless tag IDs and detector IDs only, it is possible to prevent medical information of the hospital 101 or the other facility from leaking out to the outside.

Thus, according to an information processing apparatus in the present disclosure, it is possible to provide positional information and medical information by using a medical information management system and an external positional information management system while preventing the medical information from leaking out.

RELATED-ART DOCUMENTS

Patent Documents

[Patent Document 1] Japanese Laid-open Patent Publication No. 2009-198209
[Patent Document 1] Japanese Laid-open Patent Publication No. 2005-173723

The present application claims priority under 35 U.S.C. § 119 to Japanese Patent Application No. 2015-173019, filed on Sep. 2, 2015, the contents of which are incorporated herein by reference in their entirety.

What is claimed is:

1. An information processing apparatus connected with an external server apparatus via a network, the external server apparatus storing identification information of a plurality of wireless apparatuses in a facility, and information about a plurality of detector apparatuses that detect identification information of the wireless apparatuses, the information processing apparatus comprising a circuitry, in communication with a memory, executing steps of:

storing, in a memory that is located in a local area network of the facility, the identification information of a wireless apparatus attached to a patient in the facility and medical information including a schedule of treatment for the patient and a condition of the patient so as to associate the identification information of the wireless apparatus with the medical information;

obtaining detection information including the identification information of the wireless apparatus, a time when the identification information of the wireless apparatus is received and the information including identification information of the detector apparatus from the external server apparatus that is configured to store detection history information including the identification information of the wireless apparatus, identification information of the detector apparatus, and the time when the identification information of the wireless apparatus is received;

generating, based on floor information that associates a floor layout of a facility, the identification information of the detector apparatus, and a location of the detector apparatus in the floor layout, and the obtained detection information, positional information of the wireless apparatus that associates a time when the patient corresponding to the wireless apparatus is detected with a detection location of the wireless apparatus in the floor layout; and providing information that is generated at a predetermined time of a detection of the wireless apparatus so as to associate a location of the patient corresponding to the identification information of the wireless apparatus with the medical information of the patient in the floor layout, based on the generated information and the medical information, to an apparatus connected to the information processing apparatus via the network, wherein the information processing apparatus is located in the local area network of the facility and connected with the external server apparatus located outside the local area network via the network, and the external server apparatus stores only the identification information of the wireless apparatus, the time when the identification information of the wireless apparatus is received and the information about the detector apparatus.

2. The information processing apparatus according to claim 1, wherein the providing provides information that represents a position of the patient, and information about the medical condition of the patient.

3. The information processing apparatus according to claim 1, wherein the providing provides information that represents a position of the patient, and information about a time when the patient receives the medical care.

4. The information processing apparatus according to claim 1, wherein the information about the medical care of the patient includes information about a place where the medical care is to be given, wherein the providing provides information for determining whether a patient located at the place where the medical care is to be given, is the patient to be given the medical care.

5. The information processing apparatus according to claim 4, wherein the circuitry executes steps of obtaining and storing of positional information of a wireless apparatus attached to a person engaged in medical care in the facility so as to manage the positional information of the wireless apparatus attached to the person engaged in the medical care.

6. The information processing apparatus according to claim 5, wherein the storing the identification information of the wireless apparatus further stores the identification information of the wireless apparatus attached to the person engaged in the medical care giving the medical care to the patient, wherein the providing provides information for determining whether a person located at a place where a medical care is to be given, is a person who is engaged in the medical care.

7. The information processing apparatus according to claim 4, wherein the circuitry executes steps of obtaining and storing the positional information of a wireless apparatus attached to a drug in the facility so as to manage the positional information of the wireless apparatus attached to the drug.

8. The information processing apparatus according to claim 7, wherein the storing of the positional information of the wireless apparatus attached to the drug further stores identification information of a wireless apparatus attached to a drug to be used for the medical care of the patient, wherein the providing provides information for determining whether a drug located at a place where the medical care is to be given, is a drug to be used for the medical care of the patient.

9. The information processing apparatus according to claim 4, wherein the storing of the positional information of the wireless apparatus stores the positional information of a wireless apparatus attached to a device in the facility so as to manage the positional information of the wireless apparatus by using the information of the detector apparatus obtained by the obtaining.

10. The information processing apparatus according to claim 9, wherein the storing of the positional information of the wireless apparatus attached to the device further stores identification information of a wireless apparatus attached to a device to be used for the medical care of the patient, wherein the providing provides information for determining whether a device located at the place where the medical care is to be given, is the device to be used for the medical care of the patient.

11. The information processing apparatus according to claim 1, wherein the providing transmits the information about medical care of the patient to an information terminal connected to the information processing apparatus via a network.

12. The information processing apparatus according to claim 1, wherein the providing transmits the information about medical care of the patient to a display apparatus connected to the information processing apparatus via a network.

13. The information processing apparatus according to claim 1, wherein the wireless apparatus is an active RFID tag to transmit the identification information of the wireless apparatus.

14. The information processing apparatus according to claim 1, wherein the information about the detector apparatus represents identification information to identify the detector apparatus.

15. The information processing apparatus according to claim 1, wherein the information about the detector apparatus represents positional information to identify a position of the detector apparatus.

16. The information processing apparatus according to claim 1, wherein the storing of the positional information of the wireless apparatus associates the information obtained by the obtaining, with information to identify a position at which the detector apparatus is installed, to generate the positional information of the wireless apparatus.

17. An information processing system, comprising:

an external server configured to store identification information of a plurality of wireless apparatuses in a facility, and information about a plurality of detector apparatuses that detect identification information of the wireless apparatuses, the external server being provided outside of the facility; and the information processing apparatus according to claim 1 that is disposed in the facility, and connected with the external server apparatus via the network.

18. The information processing apparatus according to claim 1, wherein the circuitry further executes a step of:

acquiring information about a place where a call operation has been made in the facility, wherein the providing further provides the information about the place where the call operation has been made in the facility along with the information including the medical condition of the patient by which a user of the information processing apparatus determines a level of emergency of the call operation.

19. The information processing apparatus according to claim 1, wherein the external server apparatus receives only the identification information of the wireless apparatus, and the information about the detector apparatus that are transmitted from the detector apparatus with a predetermined interval.

20. An information processing system including an information processing apparatus connected with an external server apparatus via a network, the external server apparatus storing identification information of a plurality of wireless apparatuses in a facility, and information about a plurality of detector apparatuses that detect identification information of the wireless apparatuses, the information processing system comprising a circuitry, in communication with a memory, executing steps of:

storing, in a memory that is located in a local area network of the facility, the identification information of a wireless apparatus attached to a patient in the facility and medical information including a schedule of treatment for the patient and a condition of the patient so as to associate the identification information of the wireless apparatus with the medical information;

obtaining detection information including the identification information of the wireless apparatus, a time when the identification information of the wireless apparatus is received and the information including identification information of the detector apparatus from the external server apparatus that is configured to store detection history information including the identification information of the wireless apparatus, identification information of the detector apparatus, and the time when the identification information of the wireless apparatus is received;

generating, based on floor information that associates a floor layout of a facility, the identification information of the detector apparatus, and a location of the detector apparatus in the floor layout, and the obtained detection information, positional information of the wireless apparatus that associates a time when the patient corresponding to the wireless apparatus is detected with a detection location of the wireless apparatus in the floor layout; and providing information that is generated at a predetermined time of a detection of the wireless apparatus so as to associate a location of the patient corresponding to the identification information of the wireless apparatus with the medical information of the patient in the floor layout, based on the generated information and the medical information, to an apparatus connected to the information processing apparatus via the network, wherein the information processing apparatus is located in the local area network of the facility and connected with the external server apparatus located outside the local area network via the network, and the external server apparatus stores only the identification information of the wireless apparatus, the time when the identification information of the wireless apparatus is received and the information about the detector apparatus.

21. A method for providing information, executed by an information processing apparatus connected with an external server apparatus via a network, the external server apparatus storing identification information of a plurality of wireless apparatuses in a facility, and information about a plurality of detector apparatuses that detect identification information of the wireless apparatuses, the method comprising:

storing, in a memory that is located in a local area network of a facility, the identification information of a wireless apparatus attached to a patient in the facility and medical information including a schedule of treatment for the patient and a condition of the patient so as to associate the identification information of the wireless apparatus with the medical information;

obtaining detection information including the identification information of the wireless apparatus, a time when the identification information of the wireless apparatus is received and the information including identification information of the detector apparatus from the external server apparatus that is configured to store detection history information including the identification information of the wireless apparatus, identification information of the detector apparatus, and the time when the identification information of the wireless apparatus is received;

generating, based on floor information that associates a floor layout of a facility, the identification information of the detector apparatus, and a location of the detector apparatus in the floor layout, and the obtained detection information, positional information of the wireless apparatus that associates a time when the patient corresponding to the wireless apparatus is detected with a detection location of the wireless apparatus in the floor layout; and providing information that is generated at a predetermined time of a detection of the wireless apparatus so as to associate a location of the patient corresponding to the identification information of the wireless apparatus with the medical information of the patient in the floor layout, based on the generated information and the medical information, to an apparatus connected to the information processing apparatus via the network, wherein the information processing apparatus is located in the local area network of the facility and connected with the external server apparatus located outside the local area network via the network, and the external server apparatus stores only the identification information of the wireless apparatus the time when the identification information of the wireless apparatus is received and the information about the detector apparatus.

* * * * *